United States Patent
Claus et al.

(10) Patent No.: US 6,862,337 B2
(45) Date of Patent: Mar. 1, 2005

(54) LINEAR TRACK BASED DIGITAL TOMOSYNTHESIS SYSTEM AND METHOD

(75) Inventors: Bernhard Erich Hermann Claus, Niskayuna, NY (US); Beale Opsahl-Ong, Darien, CT (US); Mehmet Yavuz, Plano, TX (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/607,569

(22) Filed: Jun. 25, 2003

(65) Prior Publication Data

US 2004/0264636 A1 Dec. 30, 2004

(51) Int. Cl.[7] ............................................. G01N 23/083
(52) U.S. Cl. ............................. 378/26; 378/23; 378/22
(58) Field of Search ............................... 378/21, 22, 23, 378/25, 26

(56) References Cited

U.S. PATENT DOCUMENTS 4,903,204 A * 2/1990 Dobbins, III ............... 382/255
5,872,828 A 2/1999 Niklason et al. ............. 378/23
6,196,715 B1 * 3/2001 Nambu et al. .............. 378/197

OTHER PUBLICATIONS

"Fourier Based Method, Apparatus, and Medium for Optimal Reconstruction in Digital Tomosynthesis," Bernhard E. H. Claus et al.

"Method, Apparatus, and Medium for Calibration of Tomosynthesis System Geometry Using Fiducial Markers With Non–Determined Position," Bernhard E. H. Claus et al.

* cited by examiner

Primary Examiner—David V Bruce
(74) Attorney, Agent, or Firm—Jean K. Testa; Patrick K. Patnode

(57) ABSTRACT

A digital tomosynthesis system acquires a plurality of projection radiographs of an object and reconstructs structures of the object based on the acquired projection radiographs. The digital tomosynthesis system includes an x-ray source and a detector. The x-ray source emits a beam of x-rays, and moves in a linear trajectory relative to the detector.

22 Claims, 11 Drawing Sheets

LINEAR TRACK BASED DIGITAL TOMOSYNTHESIS SYSTEM AND METHOD

BACKGROUND OF THE INVENTION

Tomosynthesis reconstructs structures existing within an imaged object from a set of projection radiographs. These structures include, for example in medical applications, anatomical structures such as organs, blood vessels, and bones. In computed tomography both an x-ray source (which is also referred to as a tube) and a detector move on a circular trajectory around a common axis and a very high number of projection radiographs (or images) is acquired. That is, in computed tomography, the x-ray source and detector typically describe either a full circle around the object or a half-circle for each, x-ray source and detector. In conventional motion tomography, the x-ray source describes an arc essentially on one side of the object and the detector (or film) describes a corresponding arc (in the opposite direction) on the opposite side of the object, while one horizontal slice through the object remains in focus. In contrast, in tomosynthesis, relatively few radiographs are acquired for varying x-ray source positions. Tomosynthesis, then, is a system and method that acquires a plurality of projection radiographs, where the x-ray source assumes positions that are essentially on one side of the object, while the detector (or film) assumes positions on the opposite side of the object.

A digital tomosynthesis system comprises an x-ray source and a digital detector which are connected to each other by an appropriate mechanical structure. Generally, a number of 2-dimensional projection radiographs of a stationary imaged object is acquired at different positions of the x-ray source relative to the imaged object, and from the data sets corresponding to the 2-dimensional projection radiographs, the 3-dimensional structure of the imaged object is reconstructed.

Conventional tomosynthesis systems are not optimally suited to the "natural" pixel grid on the detector, which is apparent because the employed reconstruction techniques usually require a data interpolation step before the actual reconstruction is carried out. This interpolation step brings with it an irreversible loss in resolution, i.e., fine details (small structures) are lost before the 3D reconstruction even begins.

BRIEF SUMMARY OF THE INVENTION

In one embodiment of the invention, a digital tomosynthesis system and method are adapted to acquire a plurality of projection radiographs of an object. The system comprises an x-ray source adapted to emit a beam of x-rays and a digital detector disposed in a spatial relationship to the x-ray source relative to the object. A processor is adapted to control the x-ray source and process data from the detector such that the projection radiographs are acquired at different positions of a focal spot of the x-ray source along a linear trajectory relative to the detector.

DETAILED DESCRIPTION OF THE INVENTION

As used herein, the terms "adapted to", "configured to" and the like refer to the components that are arranged to provide a desired function as might be known to one skilled in the art. For example, in the situation of the processing of signals, data and the like, the term "adapted to" refers to a component such as a preprogrammed digital computer, an application-specific integrated circuit (ASIC), or other electronic, analog or optical computing device that can be prepared to process input signals in accordance with a desired algorithm to provide a desired output signal. In the situation of a mechanical or electromechanical device, the term "adapted to" refers to the components being assembled, connected or disposed in an operational relationship so as to provide a desired functionality, make up or arrangement in a device.

Throughout the description of the present invention, reference is made to the x-ray source being "above the detector", or a "constant height above the detector". This reference is made for clarity of explanation, and means that the x-ray source is positioned opposite to the detector relative to the imaged object and merely explains the relative positions of the x-ray source and the detector (or detector plane). Reference to the x-ray source being "above the detector" does not imply that the x-ray source is necessarily positioned "higher than the detector" since the present invention can be implemented successfully, for example, if the digital tomosynthesis system is turned upside down, so long as the relative geometry of the digital tomosynthesis system remains unchanged.

Figure 1:
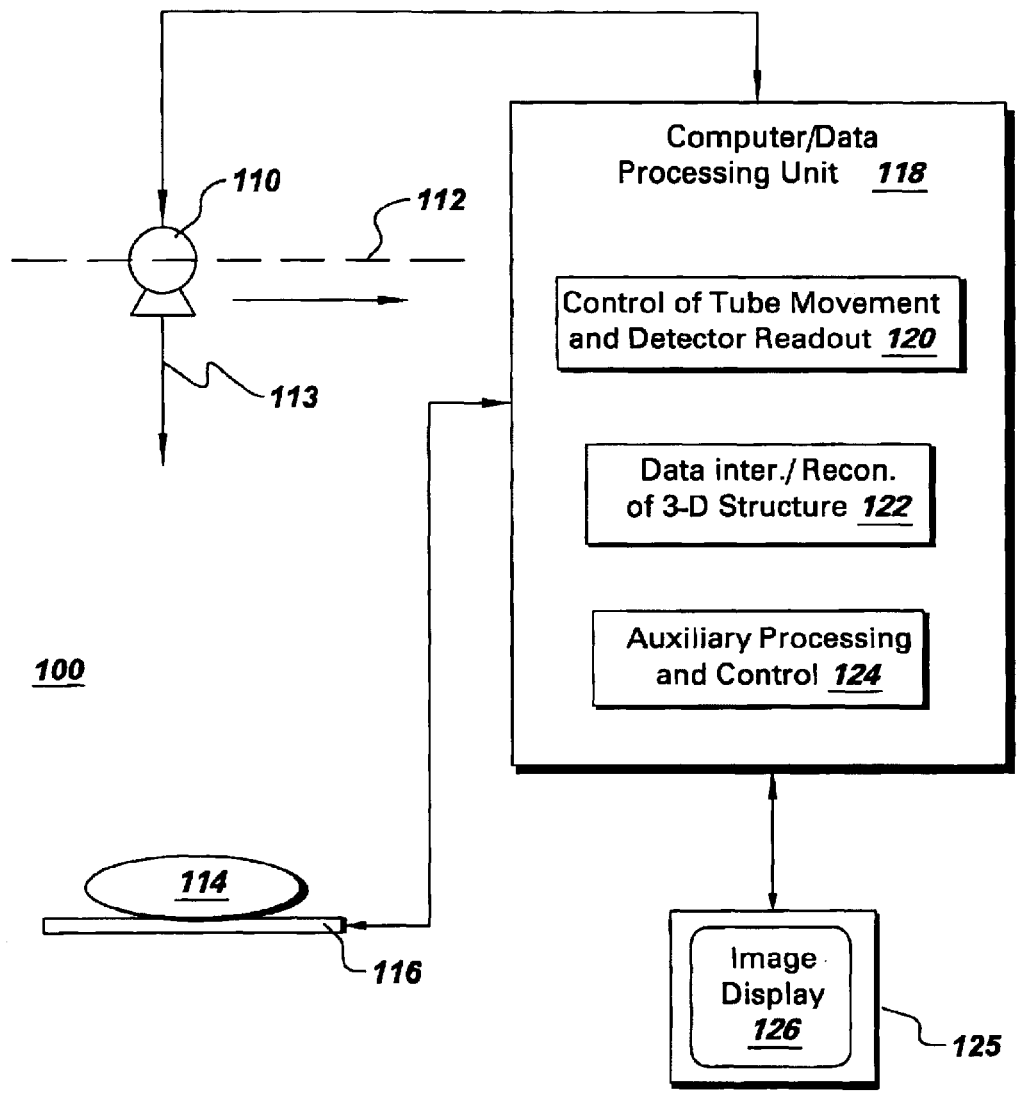
FIG. 1 shows a basic tomosynthesis system.

FIG. 1 shows a tomosynthesis system 100. As shown in FIG. 1, the tomosynthesis system 100 comprises an x-ray source (or tube) 110 that moves along a trajectory 112 and which emits x-rays 113. X-rays 113 impinge upon object (or patient) 114 and are detected by detector 116. Object (or patient) 114 contains typically 3-dimensional structures with different x-ray attenuation characteristics. Detector 116 is controlled by, and provides input to, computer/data processing unit 118.

Also as shown in FIG. 1, computer/data processing unit 118 executes processes, including controlling movement of the x-ray source 110 and readout of the detector 116, interpolating data from the detector 116 and reconstructing a 3-dimensional image of the object 114 from data (projection radiographs) detected by the detector 116, and other, auxiliary processing and control functions 124.

Thus, for a stationary object (or patient) 114, the digital tomosynthesis system 100 acquires several projection radiographs in which the position of the x-ray source 110 changes relative to the detector 116 and the object 114. Typically, this is accomplished by moving the x-ray source 110 and/or the detector 116 relative to each other and relative to the object 114 between acquisitions. From the acquired projection radiograph images, computer/data processing unit 118 reconstructs 3-dimensional information about the imaged object 114, and displays the resulting, reconstructed images. Typically, control and 3-dimensional reconstruction are performed within the computer/data processing unit 118, and the reconstructed image is displayed on a separate, specialized computer 125 with a display screen 126.

After reconstructing the 3-dimensional structure of the imaged object from data detected by the detector 116, computer/data processing unit 118 provides that reconstruction data to image display 126, which displays the reconstructed, 3-dimensional image to an operator.

In one example of conventional motion tomography, an x-ray source moves synchronously with a film such that the projection of a particular plane (the so-called "pivot plane") in the object remains stationary relative to the film during exposure. As a consequence the pivot-plane appears to be in focus while all other structures of the imaged object are "blurred". An underlying principle of this example of conventional motion tomography is that the imaging plane (i.e., the film) and the pivot plane are parallel, and that the movement of the x-ray source is also within a plane, which is parallel to the first two planes. This arrangement ensures that structures in the pivot plane are mapped onto the film with a constant magnification factor. Therefore, all one needs to do to keep the image of (structures located in) the pivot plane in focus is to move the film such that the relative position of the projections of structures inside the pivot plane remains unchanged during the movement of the x-ray source.

In conventional motion tomography, the specific trajectory of the x-ray source (as long as it is located in the aforementioned plane) has no significant impact on the "quality" with which the structures in the pivot plane appear on the film. The specific trajectory does, however, have a direct and significant impact on the way out-of-plane structures appear in the image. Generally, the larger the range of the x-ray source movement, the more pronounced the blurring of out-of-plane structures. Further, the "shape" of the source trajectory translates directly into the "shape" of the blurring. For a linear trajectory, the out-of-plane structures are blurred only along a single direction, while for a circular trajectory, the out-of-plane structures are blurred in a "circular blurring".

In two common cases of conventional motion tomography, the x-ray source moves either linearly or circularly. The first case offers the advantage of a relatively straightforward construction of a mechanical structure which connects the x-ray source support and the film support, thereby ensuring that the pivot plane is in focus throughout the whole exposure. The circular trajectory option is less attractive from the mechanical implementation standpoint, but it offers an image quality which may be perceived as being superior to the linear trajectory option. The reason for this is that the "linear blur" creates streak artifacts which are easily misinterpreted as being significant structures in the pivot plane. This problem may be considered to be less severe for the circular trajectory case, where the blurring appears in circular form.

Some conventional motion tomography systems include a constraint that the x-ray source is at a constant distance from the film/detector, which means that the x-ray source is located in a plane that is parallel to the detector plane during the whole data acquisition process. That constraint does not apply to other conventional tomography systems or to digital tomosynthesis systems. However, in conventional tomography systems, the movement of the x-ray source and detector/film are carefully synchronized, which is not required for digital tomosynthesis.

An identical approach as mentioned above can be employed when using a digital detector instead of film, although typically images are taken at discrete instants in time for multiple discrete x-ray source (or tube) locations, and during each exposure both x-ray source and detector remain stationary. However, due to the increased versatility of a digital system the same set of projection images can be used not only to reconstruct the structures located in the pivot-plane, but also to reconstruct a "slice" through the imaged object at any arbitrary height. As used herein, the term "slice" refers to a planar cross-section through the imaged object, or planar cross-section through the volume to be reconstructed, where the cross-section is taken along a plane that is parallel to the detector plane. Furthermore, the additional flexibility afforded by a digital tomosynthesis system enables the development of other system concepts as well, such as where, the x-ray source assumes discrete positions along a circular arc above the detector. Unlike in the circular tomosynthesis case, in such a system, the circular arc lies in a plane which is perpendicular to the detector plane.

One technique for reconstructing slices from images captured by a digital tomosynthesis system is referred to as "shift and add". The "shift and add" technique is substantially equivalent to the image formation process in conventional motion tomography. With a discrete number of image exposures involved in digital tomosynthesis, a simple "shift and add" operation shifts (and scales, if necessary), then sums different projection radiographs captured by the digital tomosynthesis system. Selection of an appropriate shift for each projection image allows the digital tomosynthesis system to focus on a logical plane (i.e., slice) existing at an arbitrary height within the object. That is, the "shift and add"

technique of image reconstruction results in images in which out-of-plane structures appear "blurred" (i.e., they appear in the form of several low-contrast copies which are shifted with respect to each other), and the degree of blur of the out-of-plane structures depends upon their distance from the pivot plane, or reconstructed slice.

Figure 2:
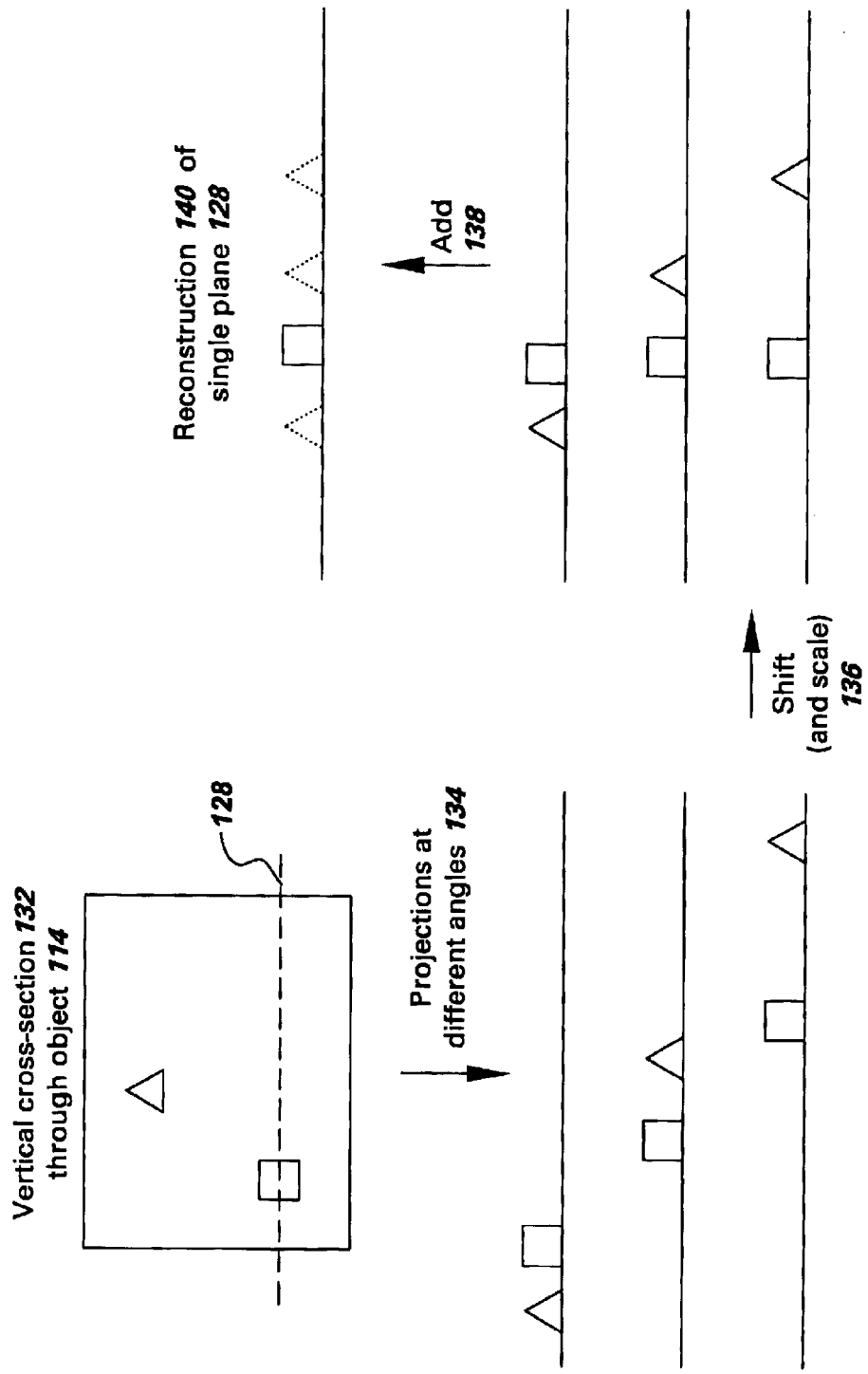
FIG. 2 illustrates flow showing the principle of a "shift and add" reconstruction approach.

FIG. 2 illustrates flow 130 showing the principle of the above-mentioned "shift and add" reconstruction approach. As shown in FIG. 2, object 114 includes a structure (represented by a square) located on plane 128 of the object 114, and another structure (represented by a triangle) located on a plane different than plane 128 in object 114. For the purpose of illustration, vertical cross-section 132 is assumed to be located in a plane which contains the trajectory of the x-ray source (or tube), as well as the two structures located within the object 114. This vertical cross-section 132 results in projections 134 at different angles of the x-rays 113 (i.e., at different positions of the x-ray source) being detected by detector 116. These projections 134 are then transmitted to computer/data processing unit 118, which executes various processes on the projections 134 by the data interpolation/reconstruction process 122. These processes include shifting and scaling 136 of the detected projections, adding (or averaging) 138 of the result, thereby obtaining a reconstruction 140 of a single plane 128 (which includes the structure indicated by the square). Any out-of-plane structures (such as the structure represented by the triangle) appear as "blurred" structures in the reconstruction. That is, for discrete positions of the x-ray source 110, several low contrast copies of the out-of-plane structures (that is, the triangle) are present in the reconstruction image (or slice) 140. This process (i.e., shifting and scaling 136 of the detected projections, and adding or averaging 138 of the result) is repeatedly performed with different shift and scaling parameters if reconstruction of a plurality of slices at different heights is desired.

The advent of digital tomosynthesis brought the following two effects. The first effect is that the mechanical structure which connects x-ray source and detector is of less importance. One can easily shift (and scale, if needed) digitally available projection images, thus the images of the plane to be reconstructed do not need to have the same position relative to the detector for different x-ray source locations. Indeed, the entire imaged three dimensional volume can be reconstructed from a single set of projection images, i.e., one does not need to acquire a new set of projection images in order to reconstruct a new plane/slice. This is a consequence of each single image being available digitally, and therefore the "shift" of each image can be adjusted such that any arbitrary plane between detector and x-ray source appears to be in focus. Consequently, the detector does not need to be moved at all (although this may be desired in order to capture the projection image of the object completely). The same underlying principle which allows one to move the detector and x-ray source independently leads to the fact that the x-ray source positions do not necessarily need to be all at the same height (i.e., in a parallel plane) above the detector, or at heights which are closely coordinated with the position of the detector. In fact, any arbitrary combination of heights can be used, and consequently the system geometry may be adapted to the specific application at hand (breast imaging, chest imaging, etc.)

The second effect, and a major difference to conventional motion tomography, is that the reconstruction methods can now go beyond the simple "shift and add" reconstruction approach (which is the equivalent to the image formation process in conventional motion tomography). With "shift and add", one sees the same type of artifacts and blurring of out-of-plane structures as in conventional motion tomography, while with more advanced reconstruction algorithms the impact of the out-of-plane artifacts can be immensely reduced. That is, a number of techniques have been developed which can be used to remove the foregoing artifacts. Typically, these techniques involve characterizing a point spread function which leads to the blur, then deconvolving the full 3-dimensional reconstruction obtained using the above-mentioned shift-and-add method, either in the spatial or the Fourier domain. The point spread function is typically assumed to be independent of the location in space, meaning that implicitly a parallel projection or similar approximation is assumed.

Another type of approach to reconstruct the three-dimensional structure of the object is based on the so-called filtered backprojection, in which each projection image is filtered before backprojecting (and summing/averaging) the projection images. This approach is based on the assumption that the x-ray source and the detector rotate around a common axis, and to be able to use that framework directly the projection images acquired with a tomosynthesis system have to be first mapped to this assumed geometry, which leads to a slight degradation in image quality. Moreover, the filtered backprojection approach yields accurate reconstructions only from "complete" data having a large number of projections from different angles of the x-ray source.

In addition, there is a technique referred to as the algebraic reconstruction technique (ART). In the algebraic reconstruction technique, the object is assumed to be represented as a linear combination of 3-dimensional basis functions. This approach leads to solving a large (although sparse) system of linear equations, which can be solved iteratively.

These algebraic reconstruction methods are sensitive to measurement noise, and the choice of the particular basis functions may lead to inconsistencies in the resulting system of linear equations.

A digital tomosynthesis system of the present invention acquires a plurality of projection radiographs of an object and reconstructs structures of the object based on the acquired projection radiographs. These structures include, for example, anatomical structures such as organs, blood vessels, and bones. The digital tomosynthesis system includes an x-ray source and a detector. The x-ray source emits a beam of x-rays. The detector is provided opposite to the x-ray source relative to the object and has pixels organized into rows and columns. The projection radiographs are acquired at different positions of the focal spot of the x-ray source relative to the object and/or detector along a linear trajectory of the x-ray source.

More particularly, the present invention comprises a digital tomosynthesis system having an x-ray source and a digital detector. In the present invention, the digital detector comprises a pixel-grid of a regular configuration, such as rectangular or hexagonal. In a rectangular pixel grid, rows and columns would form 90-degree angles, and in a hexagonal pixel grid, rows and columns would form 60-degree angles. In one embodiment of the present invention, the x-ray source moves along a linear trajectory, for example on a track. In one embodiment of the present invention, the linear trajectory is located in a plane parallel to the detector plane, and in addition the linear trajectory is parallel to a row (or column) of pixels of the detector. This specific configuration is optimally suited to the digital detector and allows, in conjunction with an appropriate irregular discretization of the imaged volume, the use of very efficient reconstruction techniques.

Figure 3:
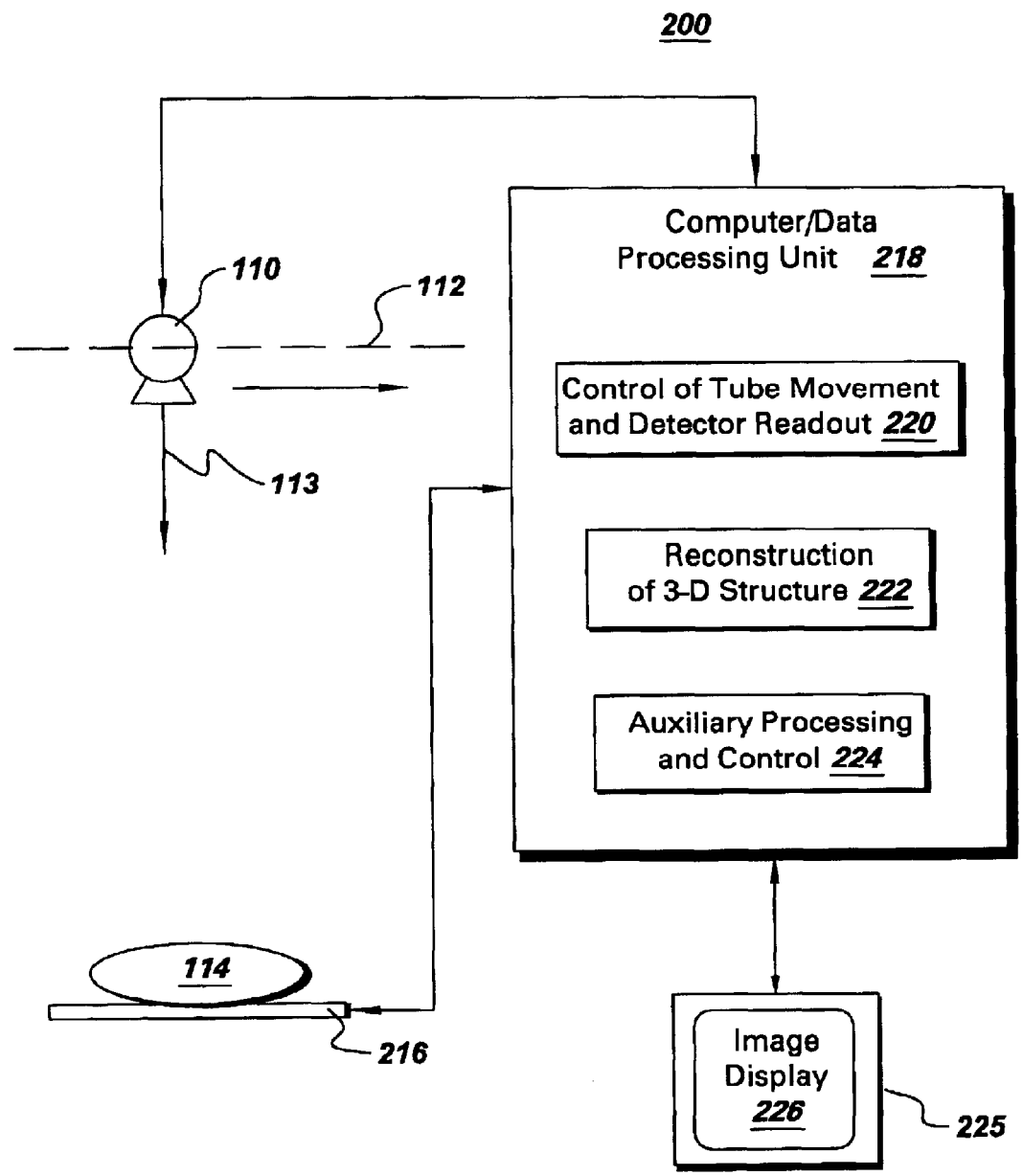
FIG. 3 shows an overview of the digital tomosynthesis system of the present invention.

FIG. 3 shows an overview of the digital tomosynthesis system 200 of the present invention. In the digital tomosynthesis system 200 of the present invention, x-ray source (or tube) 110 emits x-rays 113 which impinge upon object (or patient) 114. Also in the digital tomosynthesis system 200 of the present invention, x-ray source 110 moves along a linear trajectory 212 at an essentially constant height above the detector 216.

Figure 5:
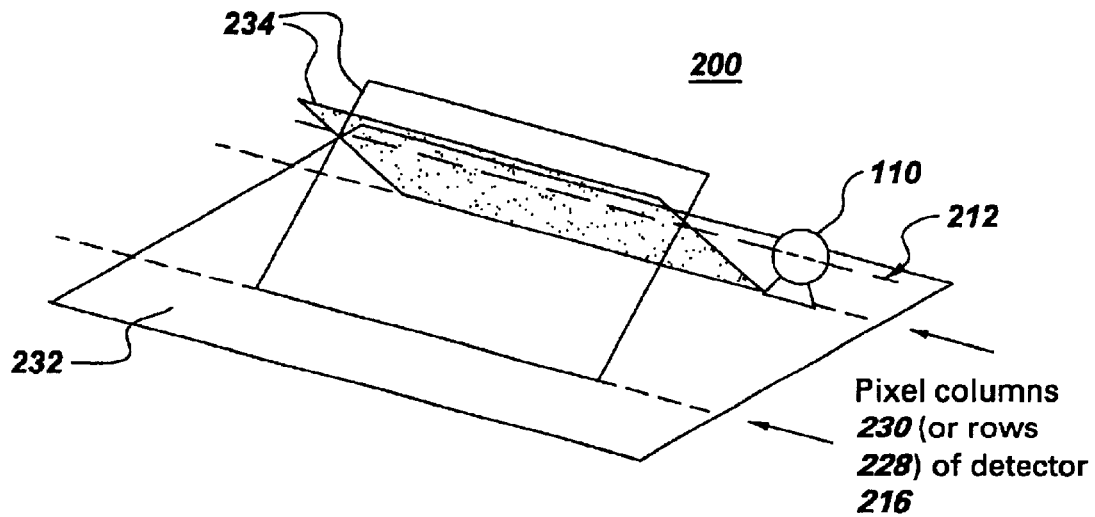
FIG. 5 shows a geometric relationship between an X-ray source, a trajectory of the x-ray source, and detector plane in the digital tomosynthesis system of the present invention.
Figure 8:
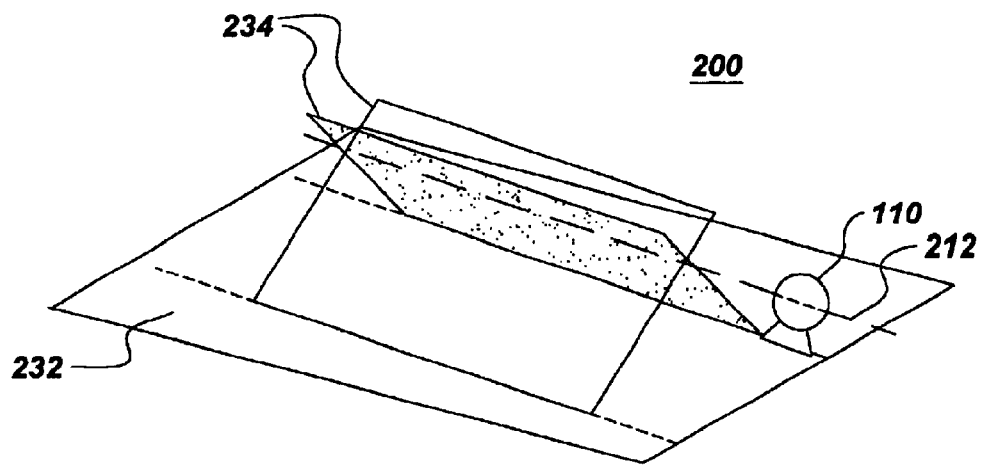
FIG. 8 illustrates another embodiment of the digital tomosynthesis system of the present invention.

Further constraints may be optionally placed upon the trajectory 212 consistent with the present invention. One of the further constraints is that the trajectory 212 (as shown in FIG. 8), is linear and is at a constant height above the detector 116, and another of the constraints is that the linear trajectory 212 is parallel to rows or columns of the detector 116, that is, there is a plane extending from the surface of the detector 216 and aligned with a row or a column of the detector element, that also contains the linear trajectory 212 (as shown in FIG. 5).

In the ensuing discussion, reference is made generally to the position of the focal spot location of the x-ray source (or tube) 110. The orientation of the x-ray source (or tube) 110 can be modified through rotation without changing the focal spot position, and the orientation of the x-ray source 110 will be adjusted typically such that the center of the emitted beam 113 is proximate to or at the center of the detector 216.

The focal spot is the location of the point-like approximation of the x-ray source 110. The focal spot is at a fixed location with respect to the elements of the x-ray source 110. For the purposes of reconstruction (discussed herein below), the focal spot represents the location of the x-ray source 110.

Thus, in one embodiment of the digital tomosynthesis system 200, x-ray source 110 is positioned by computer/data processing unit (processor) 218 to emit x-rays 113 having focal spot positions at a constant height above the detector 216.

Detector 216 detects x-rays 113 passing through object 114, and signals correspondings to the x-rays incident of the detector 216 thereto are transmitted to computer/data processing unit 218. Computer/data processing unit 218 also controls movement of the x-ray source 110. Moreover, computer/data processing unit 218 is adapted to execute various processes, including controlling 220 movement of the x-ray source 110, controlling the exposure timing and readout of the detector 216, reconstructing 222 the 3-dimensional image of the internal structure of imaged object 114, and executing 224 auxiliary processing and controls.

Moreover, in one embodiment, the reconstructed 3-dimensional image is transmitted to a separate, specialized computer 225 with a display screen 226 for display to a user. It should be recognized, however, that the display may be part of the computer 218, and not a separate workstation.

Figure 4:
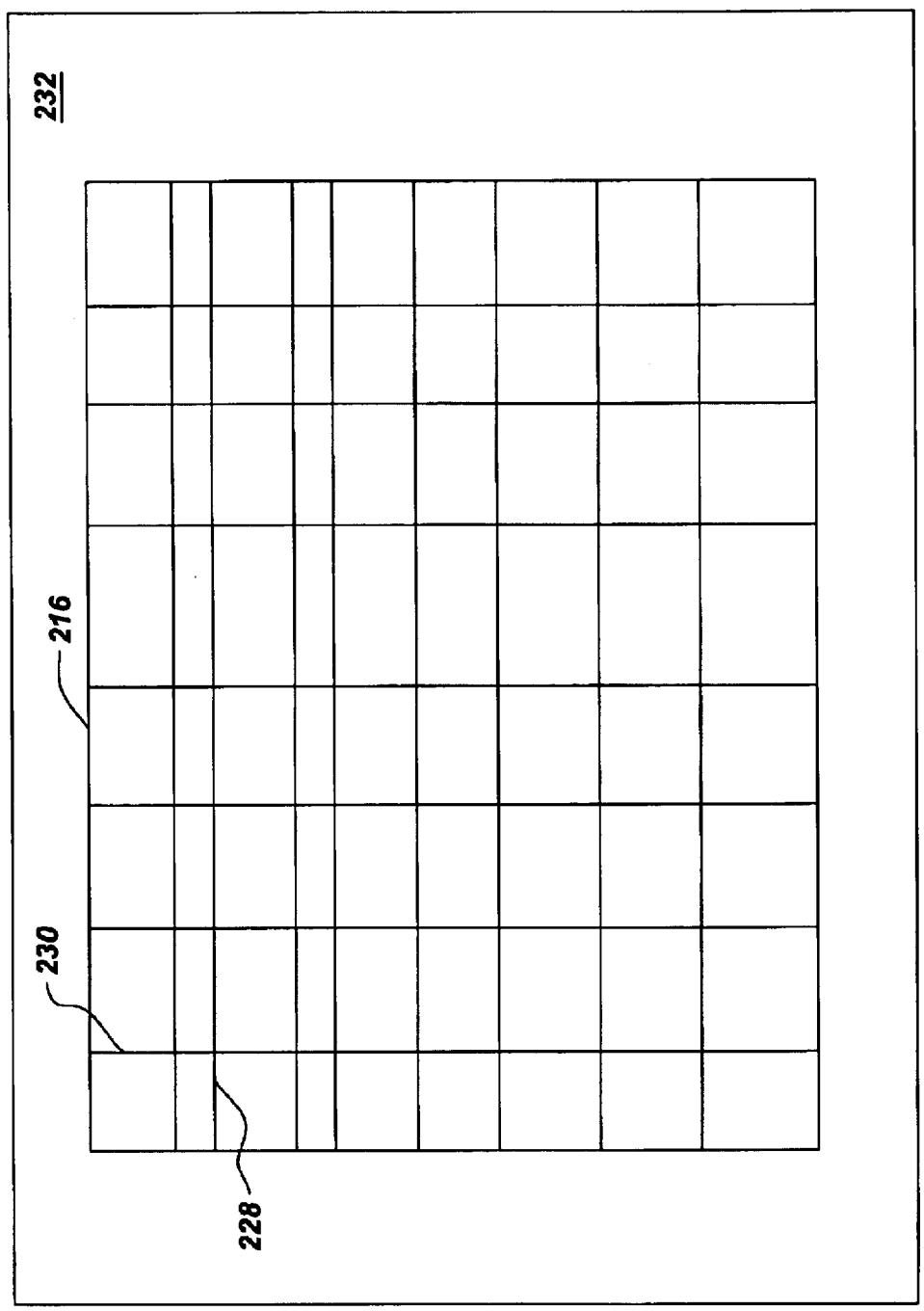
FIG. 4 illustrates a detector with a rectangular pixel-grid, i.e., having pixels organized into rows and columns in the digital tomosynthesis system of the present invention.

FIG. 4 shows detector 216 having pixels organized into rows 228 and columns 230. Moreover, FIG. 4 shows that detector 216 resides, geometrically, in a detector plane 232. In the embodiment of the detector 216 shown in FIG. 4, the rows 228 and columns 230 form right (or 90-degree) angles with each other. However, in another embodiment of the detector 216 of the present invention, the rows and columns may form 60-degree angles with each other, and thus be placed in a hexagonal configuration.

FIG. 5 shows a geometric relationship between x-ray source 110, trajectory 212 of x-ray source 110, and detector plane 232 in one embodiment of the digital tomosynthesis system 200 of the present invention. In that embodiment of the present invention, for every row 228 (or column 230) of pixels, there is a uniquely defined plane 234 (in 3-dimensions) such that for any x-ray source 110 position on the trajectory 212, all structures (of an object 114) located within that plane 234 are projected onto the corresponding pixel row 228 (or column 230).

Since the x-ray source 110 moves along a linear trajectory 212, a two-dimensional reconstruction technique for reconstructing the structure of the imaged object from the acquired images can be implemented by the computer/data processing unit 218. In particular, if one considers an arbitrary plane 234 that contains the linear trajectory 212, then this plane 234 intersects the detector plane 232 in a line (such as pixel columns 230 or pixels rows 228, in the embodiment shown in FIG. 5). All points in that plane 234 are projected onto points located on that line in the detector plane 232. This is true for any position of the x-ray source 110 on the linear trajectory 212.

On the other hand, no other point in 3-dimensional space is projected onto that line (which corresponds to pixel rows 228 or pixel columns 230 in the embodiment of FIG. 5) in the detector plane 232. Therefore, the "profiles" (or cross-sections) along that line through the different projection images contain all of the information about structures of the imaged object 114 located in that plane 234. Therefore, these profiles allow for an optimal reconstruction of the corresponding planar cross-section through the imaged object 114.

Thus, a full 3-dimensional reconstruction of the object 114 in this framework is accomplished by performing the corresponding 2-dimensional reconstructions of planar cross-sections corresponding to planes 234 which contain the x-ray source trajectory 212. The 3-dimensional structures of the object 114 arise as a natural "patchwork" of the reconstructed 2-dimensional structural information.

Moreover, in the embodiments of FIG. 5 or FIG. 8, since the trajectory 212 of the x-ray source 110 is located inside a plane that is parallel to the detector plane 232, an additional "decoupling in the Fourier domain" of the structures of the object 114 is provided as the structures appear in the projections onto the detector plane 232. All structures inside a given slice through the object 114 (which is assumed to be parallel to the detector 216) are magnified by a constant magnification factor as they appear in the projection image. The constant magnification factor is independent of the particular location of the x-ray source 110 along its trajectory 212, and is a consequence solely of the fact that the x-ray source 110 moves in a trajectory 212 inside a plane parallel to the detector 216.

Consequently, a sinusoidal "attenuative structure" in a slice through the object 114 is seen as a sinusoidal function in each of the projection images detected by the detector 216. The frequency of this projected sinusoidal function is a function of the frequency of the original structure, together with the constant magnification factor, while its phase shift depends on the particular location of the x-ray source 110.

The constant magnification factor, although independent of the particular x-ray source 110 location, does depend on the height of the considered slice through the object 114; there is a one to one relationship between the distance of the slice from the detector 216 and the associated constant magnification factor.

Therefore, when representing the projection images in terms of sinusoidal functions (using, e.g., the standard Fourier transform), then each one of these sinusoidal terms is associated with a sinusoidal function at a particular and uniquely defined frequency for each slice through the object 114. Only the sinusoidal components of the object 114 slices at these particular frequencies play a role in the formation of the considered frequency component in the projection images detected by the detector 216. This unique relationship in the Fourier domain can be used to advantage when reconstructing the 3-dimensional structure of the imaged object 114, as discussed in further detail below.

Figure 6:
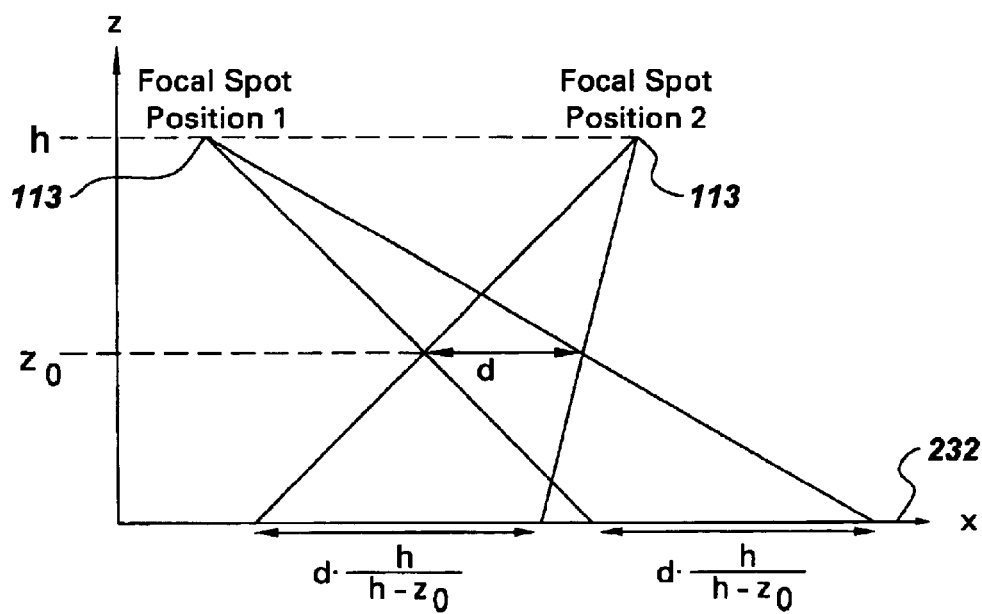
FIG. 6 illustrates the geometric relationships of the digital tomosynthesis system of the present invention which result in a constant magnification factor.

FIG. 6 shows an example of the geometric relationships of the digital tomosynthesis system of the present invention which result in the constant magnification factor:

$$\frac{h}{h-z_0}$$

Referring now to FIG. 6, x-ray source 110 (not shown in FIG. 6) moves along trajectory 212 relative to detector 216 (not shown in FIG. 6) that lies in detector plane 232. Trajectory 212 includes, for example, Focal Spot Position 1 and Focal Spot Position 2. The magnification factor for structures included in object 114 at a given height $z_o$ is constant for all Focal Spot Positions located along trajectory 212 if trajectory 212 is included in a plane which is parallel to the detector plane 232. That is, each x-ray beam 113 that is emitted by x-ray source 110 from Focal Spot Position 1 or from Focal Spot Position 2 (located at height h above the detector plane 232) magnifies a structure located at height $z_o$ above the detector plane 232 by the above-mentioned constant magnification factor.

Moreover, in the embodiment of a digital tomosynthesis system shown in FIG. 5, since the linear trajectory 212 of the x-ray source 110 is parallel to a column 230 or row 228 of pixels in the detector 216, it follows that the lines onto which structures located in planes which contain the x-ray source trajectory 212 are mapped, are parallel to the pixel columns 230 or rows 228 (respectively) of the detector 216. Using this property, and using an appropriate irregular (i.e., non-rectangular) "voxel-structure" (i.e., discretization of the 3-dimensional volume encompassing the object 114 to be reconstructed, see FIG. 7) the computational complexity of the required interpolations as well as the associated loss in resolution is reduced in the digital tomosynthesis system 200 of the present invention since interpolation of only one-dimensional functions, and not two-dimensional images, is performed by Reconstruction process 222. Furthermore, when using the above mentioned voxel-structure, the relative position of the points at which interpolation of the function is performed, is fixed (and the same for all points), in relation to the pixel grid of the detector, therefore the interpolation by process 222 can be computed in an efficient manner that is, less time is taken to process the interpolation for a given processor.

Moreover, using the above-mentioned property, and using the above-mentioned appropriate irregular "voxel-structure" (i.e., discretization of the 3-dimensional volume of the object 114 to be reconstructed), a significant part of the interpolation of the projected image data (that is, the data interpolation step included in process 122 shown in FIG. 1) before using the projected image data for the reconstruction is avoided.

This property is advantageous because the interpolation process that is usually part of process 122 inherently leads to a loss in resolution and therefore a loss of image quality in the digital tomosynthesis system 100 of the related art. Furthermore, performing the interpolation process included in 122 by the digital tomosynthesis system 100 of the related art commonly requires additional computations.

The data on the irregular voxel-grid for the reconstructed volume can be interpolated after performing the reconstruction step, if it is desired to display the reconstructed volume on a regular (such as a rectangular) grid.

Figure 7:
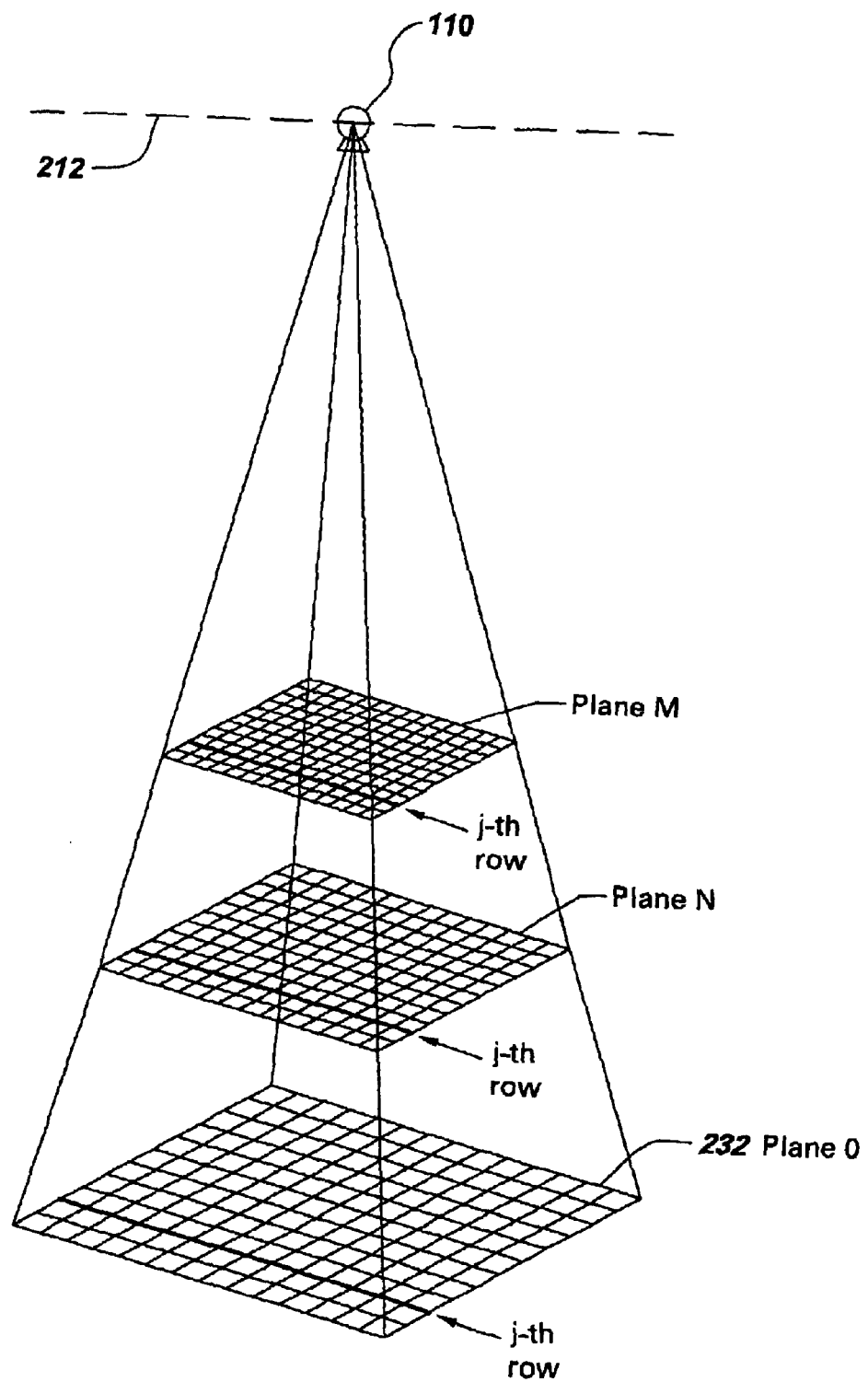
FIG. 7 shows an optimal voxel-structure (non-rectangular coordinate system) associated with the reconstruction algorithms used for the digital tomosynthesis system of the present invention.

However, by first reconstructing images of the object 114 on an irregular voxel-grid (which is optimally adapted to the geometry of the digital tomosynthesis system 200 of the present invention and to the "natural" pixel grid of the detector 216, see FIG. 7) a reconstruction of the three-dimensional structure of the object 114 is provided, without introducing, as is generally the case in the digital tomosynthesis systems of the related art, a loss of resolution even before the actual reconstruction in process 122 in FIG. 1 is carried out.

Thus, as a consequence of the above-mentioned properties, the geometry of the digital tomosynthesis system 200 of the present invention provides benefits which lead to a potentially superior image quality, and a faster computation, of the reconstruction of the imaged object 114.

FIG. 7 shows an optimal "voxel-structure" (or voxel-grid) associated with the digital tomosynthesis system 200 of the present invention. In FIG. 7, planes M and N are planes located within object 114 being imaged. Every planar slice M, N of voxels is mapped to a pixel grid on the detector 216 (not shown) located in detector plane 232 by the respective constant magnification factor corresponding to the plane M, N in which the planar slice is located. By way of example, using the j-th row of every plane, the j-th rows themselves as well as the x-ray source trajectory (in the embodiment of FIG. 5) lie within a single "reconstruction plane" (which thus also contains the corresponding cross-section through the imaged volume). Thus, the reconstruction of a 3-dimensional structure at points located on row j of any horizontal plane M, N is accomplished using a 2-dimensional reconstruction within the corresponding "reconstruction plane". The input data used for this 2-dimensional reconstruction are given by the parts of the projection images which correspond to detector pixels located in the j-th row of the detector 232 (i.e., plane 0)

The combination of a set of 2-dimensional reconstructions into a volumetric 3 dimensional reconstruction is straightforward. Depending upon particular requirements, the reconstruction may already be provided in a convenient form as indicated in FIG. 7, or for any given point in the 3-dimensional volume, an associated value of the reconstruction is computed by computing an interpolating value from the 2-dimensional reconstructions at the points closest to the considered point in the 3-dimensional volume.

The irregular voxel-grid of FIG. 7 is also useful in the method of the present invention for a general tomosynthesis system 200, where the x-ray tube assumes positions such that the focal spot positions are at a constant height above the detector (which corresponds to the embodiment shown in FIG. 8), because the horizontal spacing between voxels multiplied with the corresponding magnification factor (for that height) results in the pixel spacing of the detector. Thus, a number of interpolation processes can be avoided. In that case it may be advantageous to rotate the voxel-grid such that the rows (or columns) of voxels within a horizontal slice are parallel to the linear x-ray source trajectory.

FIG. 8 illustrates another embodiment of the digital tomosynthesis system 200 of the present invention in which the trajectory 212 of the x-ray source 110 is at a constant height above the detector plane 232, but is not parallel to the rows 228 or columns 230 of the detector 216.

Figure 9:
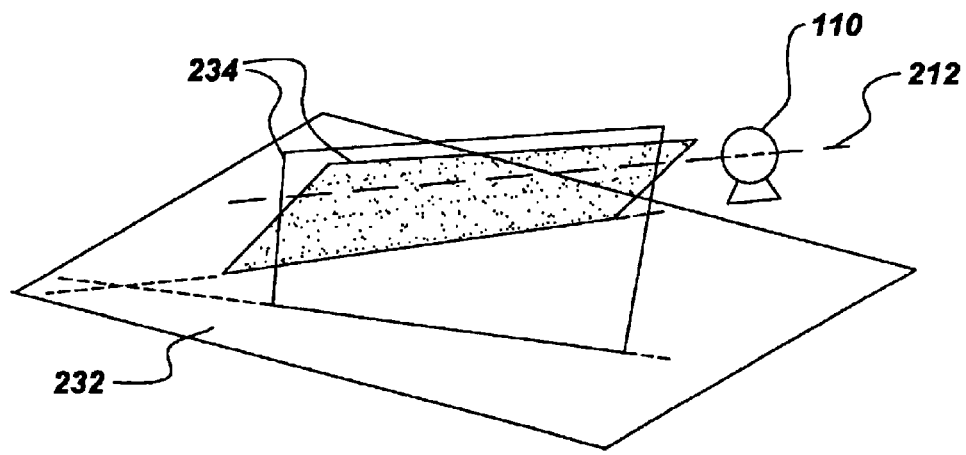
FIG. 9 illustrates an additional embodiment of the digital tomosynthesis system of the present invention.

FIG. 9 illustrates an additional embodiment of the digital tomosynthesis system 200 of the present invention in which the trajectory 212 of the x-ray source 110 is not at a constant height above the detector plane 232. Since the trajectory 212 of the x-ray source 110 is not located at a constant height above the detector plane 232, the trajectory 212 is not parallel to the rows 228 or to the columns 230 of the detector 216. In the embodiment shown in FIG. 9, a line which includes the trajectory 212 of the x-ray source 110 will intersect with the detector plane 232.

The digital tomosynthesis system of the present invention has applications in chest imaging, breast imaging, etc., as well as in other non-medical fields of application (e.g., for non-destructive evaluation).

One method for Reconstruction of 3D Structure 222 shown in FIG. 3 is now discussed. In the following method, the object 114 is reconstructed from a limited number of digital radiographic projection images. Also in the following method, the x-ray source 110 of the digital tomosynthesis system 200 assumes a number of different positions which are all located at the same height above the detector 216 (shown in FIG. 3), i.e., in one embodiment we have a digital tomosynthesis system embodiment as shown in FIG. 8 or FIG. 5. In another embodiment, the x-ray source 110 of the digital tomosynthesis system 200 assumes a number of different positions which are all located at the same height above the detector 216, but which are not located on a line. The following method, referred to as a Fourier based method for optimal reconstruction in digital tomosynthesis, uses the fact that the image acquisition process maps a sinusoidal attenuation profile in a plane through the imaged object 114 located at a selected height above the detector 216 onto a sinusoidal function that is observed in the projection image detected by the detector 216. The sinusoidal function includes a height-dependent shift in phase and frequency. Moreover, the shift in phase also depends on the location (in a horizontal coordinate system) of the x-ray source 110. The foregoing information is used to reconstruct the Fourier coefficients of horizontal slices through the object 114 from the Fourier transforms of the respective projection images.

In an additional embodiment, in the Fourier based method for optimal reconstruction in digital tomosynthesis, a constraint that the object 114 is located within a bounded volume or other suitable constraints are used to reconstruct components of the object structure which cannot be determined by the relationship in the Fourier domain alone. The above-mentioned constraints lead to an iterative procedure that provides reconstruction of an optimal estimate of the 3-dimensional structure of the imaged object 114.

The Fourier based method for optimal reconstruction in digital tomosynthesis provides high image quality as it is optimally adapted to the imaging geometry of the digital tomosynthesis system 200 (in the embodiments of FIG. 5 or FIG. 8) and to the tomosynthesis acquisition process. Moreover, the Fourier based method for optimal reconstruction in digital tomosynthesis reconstructs the image of the object 114 without introducing artifacts or degrading the image quality of the reconstruction due to inappropriate approximations (such as parallel projection).

The Fourier based method for optimal reconstruction in digital tomosynthesis provides a method for optimal image reconstruction from tomosynthesis radiographic projection images and is optimally suited to a digital tomosynthesis system geometry in which different x-ray source 110 positions are located in a plane parallel to the detector 216. Moreover, the Fourier based method for optimal reconstruction in digital tomosynthesis does not exhibits the drawbacks of the above-mentioned "shift and add", filtered backprojection, and ART techniques.

In the Fourier based method for optimal reconstruction in digital tomosynthesis, an assumption is made that the respective focal positions of the x-ray source 110 are located in a fixed plane parallel to the detector 216. In one embodiment, therefore, the x-ray source 110 moves on a straight line at a fixed height above the detector 216. It can be generalized to other trajectories located in a fixed plane parallel to the detector 216.

Also in the Fourier based method for optimal reconstruction in digital tomosynthesis, an assumption is made that a number of projection images is acquired by the digital tomosynthesis system 200, since the Fourier based method for optimal reconstruction in digital tomosynthesis involves solving a number of systems of N linear equations in N unknowns, in which N is the number of projection images.

For a digital tomosynthesis system 200 having an x-ray source 110 following a linear trajectory at a constant height above the detector, all points located on a plane that contains the linear trajectory are projected onto a line in the detector plane 232, as illustrated in FIG. 5 and FIG. 8B. Moreover, the different projection lines formed as described in the detector plane 232 are parallel to each other (and to the linear trajectory 212). That is, the projections of structures located in a plane that contains the x-ray source trajectory can be considered to be essentially 2-dimensional, and do not interfere with each other. Thus, reconstruction of 3-dimensional images for a predefined volume of the object 114 is obtained using the Fourier based method for optimal reconstruction in digital tomosynthesis by solving 2-dimensional problems of reconstructing structures in a plane from a set of projections, and combining a suitable set of 2-dimensional solutions.

The object 114 to be imaged is assumed to be adequately represented by a plurality of (thin) slices, where each slice exhibits structures that do not vary as a function of height within that slice. Consequently, each slice can be considered to be essentially a 2-dimensional structure (i.e., an image), and each cut/profile through such a slice is essentially a 1-dimensional function. Therefore, each slice can be processed with standard image processing tools. In particular, the 2-dimensional Fourier transform that decomposes the image into a sum of sinusoidal components, can be computed. Similarly, for every cut through a slice or projection image, the standard 1-dimensional Fourier transform can be computed.

Figure 10:
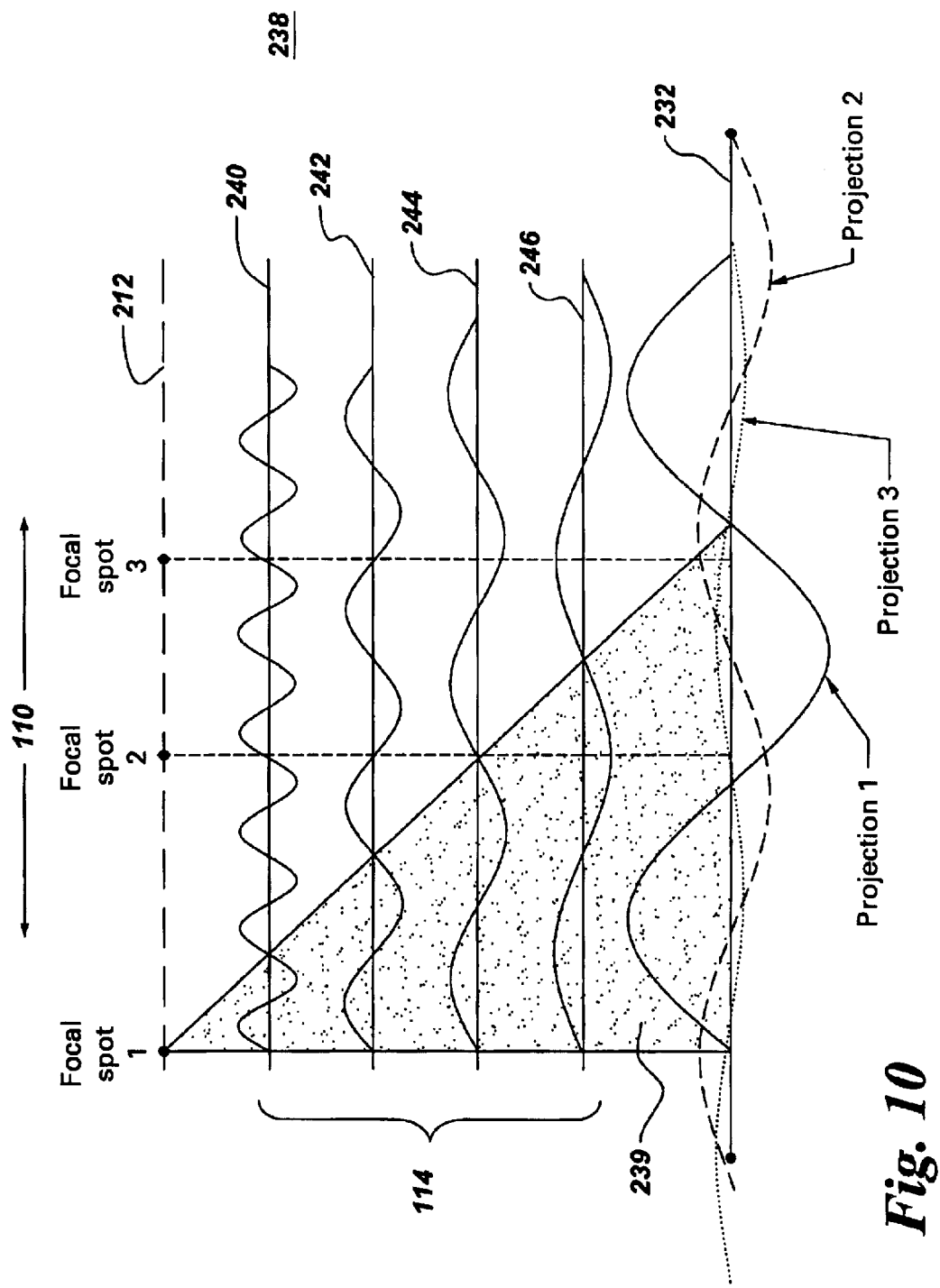
FIG. 10 illustrates a relationship between frequencies in different horizontal slices (i.e., planes parallel to the detector plane) taken of an object, and how to recover an optimal estimate of the structures within the imaged object from the projection radiographs generated by the x-ray source and the detector, in one embodiment of the digital tomosynthesis system of the present invention.
Figure 11:
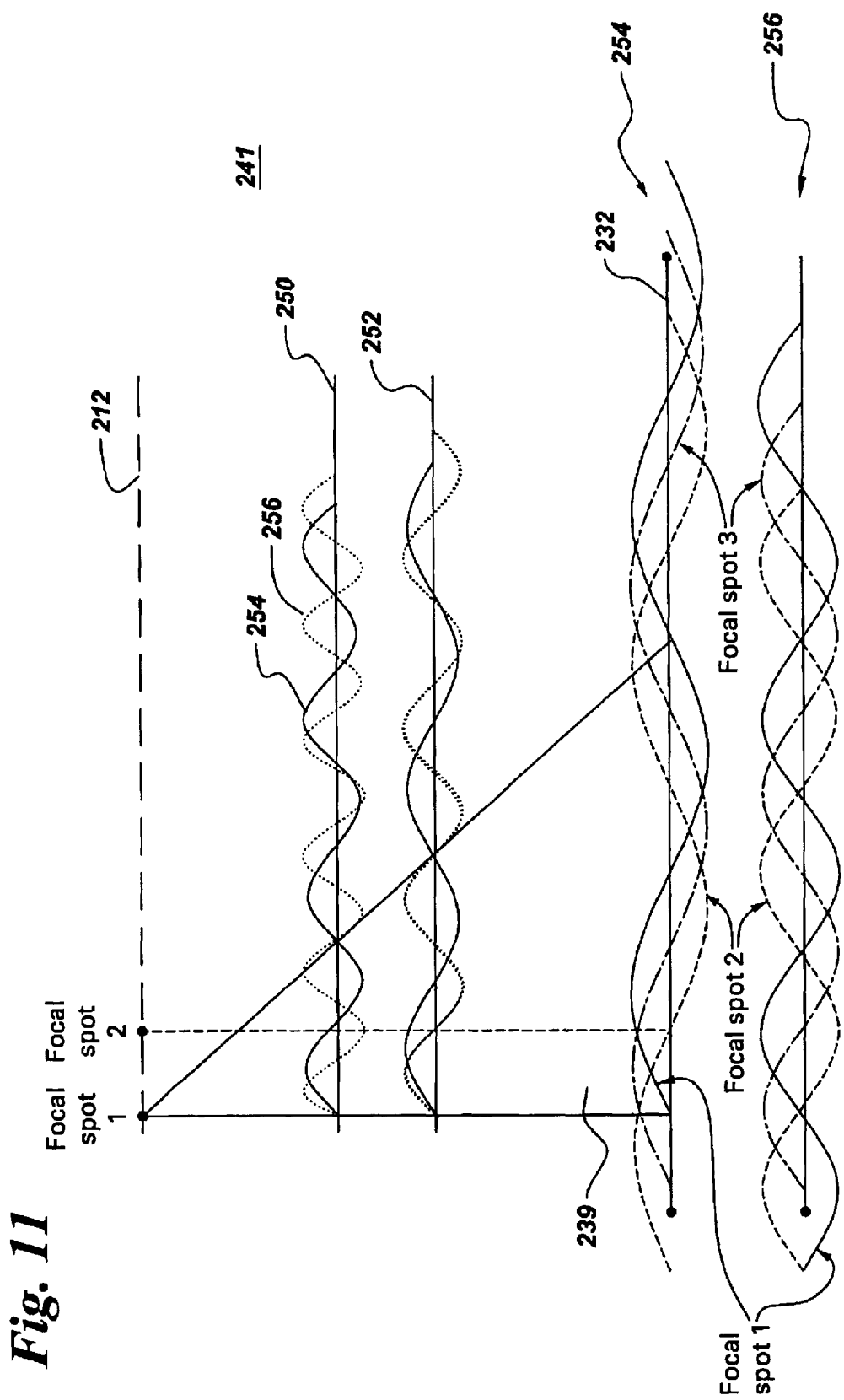
FIG. 11 illustrates the dependence of the phase shift in the projection radiographs as a function of height of a horizontal slice through the object and frequency of a sinusoidal component within that slice through the object, in one embodiment of the digital tomosynthesis system of the present invention.

FIG. 10 and FIG. 11 illustrate the principles on which the Fourier based method for optimal reconstruction in digital tomosynthesis is based. FIG. 10 illustrates a relationship 238 between frequencies of structures in different slices taken of an object, and how to recover an optimal estimate from a projection by x-ray source 110. That is, FIG. 10 is an illustration of corresponding frequencies at different heights above detector plane 232 and shows how the corresponding Fourier coefficients are linked through a system of linear equations. In particular, FIG. 10 only shows structures located in four different slices through the object. In practice, the image volume will generally be represented by a larger number of slices arranged as a "stack" of slices (without significant spacing between the slices) in order to represent the full imaged volume.

As shown in FIG. 10, x-ray source 110 emits x-rays from Focal Spots 1, 2, 3, etc., along trajectory 212 parallel to detector plane 232. The emitted x-rays travel through an object 114 having structures located on planes 240, 242, 244, and 246 parallel to detector plane 232. Each of planes 240, 242, 244, and 246 are located at a different height h above detector plane 232. That is, as shown in FIG. 10, there are structures within the object located at different planes 240, 242, 244, and 246 at different heights above, but parallel to, detector plane 232. Since the structures, and therefore planes 240, 242, 244, and 246, are located at different distances from x-ray source 110, an x-ray beam emitted by x-ray source 110 will magnify each of the structures by a magnification factor, explained herein below, as the x-ray travels through each of planes 240, 242, 244, and 246 and impinges upon detector plane 232, as shown in FIG. 10.

The relationship 238 in FIG. 10 shows an object 114 containing structures only at four different heights (i.e., the volume between these slices is assumed to be radiologically transparent). By taking the Fourier transform of the structures of object 114 within each slice, each slice is decomposed into respective sinusoidal components. FIG. 10 depicts only a single frequency component for each of the four considered slices, where, for purposes of illustration, a specific phase is assumed at each height, and furthermore these sinusoidal components are assumed to be of equal amplitude. In practice, phase and amplitude of a sinusoidal component at a given height are determined by the Fourier transform of the structures within the slice at that height.

Considering only focal spot position 1, frequencies at different heights 240, 242, 244, 246 are linked to each other by the respective magnification factor associated with each height. In particular, as illustrated by the shaded area 239 in FIG. 10, a full cycle of the sinusoidal structures indicated at each level 240, 242, 244, 246 is projected onto a full cycle at the detector plane 232. That is, for a given frequency (at the detector plane 232) there is exactly one frequency at each height 240, 242, 244, 246, which is mapped to that frequency by the projection. This simple relationship is governed by the magnification factor associated with each height 240, 242, 244, 246. In particular, this same relationship between frequencies at different heights holds for any focal spot position located on the trajectory 212. Further, an equivalent relationship holds for structures located within slices at other heights.

Further, in relationship 238 a projection image at the detector is shown as the sum of the respective projected sinusoids (at the corresponding magnified frequency) at each height 240, 242, 244, 246. For focal spot position 1 the projections of the sinusoids are all practically identical, i.e., they have the same frequency, phase, and amplitude, and thus this frequency is amplified in the resulting projection image detected by detector 216.

Referring again to FIG. 10, for focal spot position 2, due to the fact that there is the same magnification factor, the sinusoidal components are mapped onto a sinusoidal component of the projection image, which has the same frequency as the corresponding projection with respect to focal spot position 1. However, the sinusoids from the two highest slices 240, 242 cancel each other out in the projection image, and consequently the projection image detected by detector 216 contains a sinusoid of the same frequency as the projection image associated with focal spot position 1, but with a different phase and a smaller amplitude than was obtained for focal spot 1.

For focal spot position 3, an even smaller amplitude is detected by detector 216. Mathematically, the complex amplitude (i.e., amplitude and phase) of the sinusoid observed at the detector 216 is a linear combination (with complex weights of absolute value one) of the complex amplitudes of the corresponding frequency components at the different heights 240, 242, 244, 246 of the structures within the object 114. In the example illustrated in FIG. 10, this leads to a system of three (equal to the number of focal spot positions) linear equations in four (equal to the number of present slices) unknowns. This system of linear equations is underdetermined, because there are more variables than equations, but an optimal estimate of the solution is determinable. For every focal spot position of the x-ray source, and for every frequency, there is a set of weights (which are complex and of absolute value one) that are associated with the set of considered slices. For each considered focal spot position, these weights can be collected into a vector (which is referred to as "characteristic vertical profile", since every element of the vector corresponds to a different height). The optimal solution (referred to as the "optimal profile") is then determined as the set of coefficients that lies in the vector space spanned by the characteristic vertical profiles, and which satisfies the projection equations. As such, the linear combination of the characteristic vertical profiles that determines the coefficients in the optimal profile is determined by this procedure. The sum of coefficients in the optimal vertical profile, each weighted with the corresponding value of a characteristic vertical profile gives, for the corresponding focal spot, the correct Fourier coefficient of the corresponding projection at the corresponding frequency. Similar as the characteristic profile, the optimal profile is a vector containing coefficients, where each coefficient corresponds to a different height, and indicates the optimal estimate of the coefficient of the Fourier transform of structures within the slice at the corresponding height at the corresponding frequency.

In the example of FIG. 10, the optimal estimate of the vertical Fourier coefficient profile through the object 114 is given as the four-element vector which lies in the space vector spanned by the characteristic vertical profiles associated with each of the focal spots, and which satisfies the projection equations, i.e., the scalar product of the optimal profile with the characteristic profiles has the value of the corresponding complex amplitude of the Fourier coefficient of the respective projections. These relations are presented in their most general form in equations (3)(5) disclosed herein below. Note that such a relationship holds for every considered frequency, and that the characteristic vertical profiles vary as a function of the considered frequency.

FIG. 11 illustrates relationship 241 which shows that the phase shift is a function of height and frequency of a sinusoidal component. More particularly, FIG. 11 shows two sets of structures of object 114 of respective corresponding frequencies at two different planes 250, 252 (located at different heights above detector plane 232).

More particularly, FIG. 11 illustrates relationship 241 showing how the translation (and magnification) associated with the projection mapping corresponds to a phase shift for sinusoidal components, and how this (relative) phase shift depends on the height of the planes 250, 252 and the frequency 254, 256 of the structure within object 114 (not shown in FIG. 11) as well as the distance between focal spots 1 and 2.

FIG. 11 depicts two sets of sinusoidal structures of respective corresponding frequencies 254, 256 at planes at two different heights 250, 252. Structures corresponding to frequency 1 (254) are indicated by solid lines, and structures corresponding to frequency 2 (256) are indicated by dotted lines. For clarity, the resulting projections for the different frequencies 254, 256 are shown separately. For both frequencies 254, 256, the solid bold line indicates the projections resulting from focal spot 1 (the projections coincide for the respective structures at both heights 250, 252). The dashed line indicates the projection of the upper plane 250 structure with respect to focal spot 2, while the dash-dotted line indicates the projection of the lower plane 252 structure with respect to focal spot 2. The (relative) phase shift (which is proportional to the translation divided by the cycle length) increases:

with increasing distance between focal spots,
with increasing height of the position of the sinusoidal structure (above the detector 216),
with increasing frequency.

These relationships illustrate the underlying principle that helps to establish equation (2), below. That is, for a given focal spot location, and a given frequency, the phase shift depends only on the height above the detector 216 at which the considered structure is located. For different focal spot positions, this relationship changes, a fact that is used to recover information about phase and amplitude of structures of a given frequency at a given height.

Figure 12:
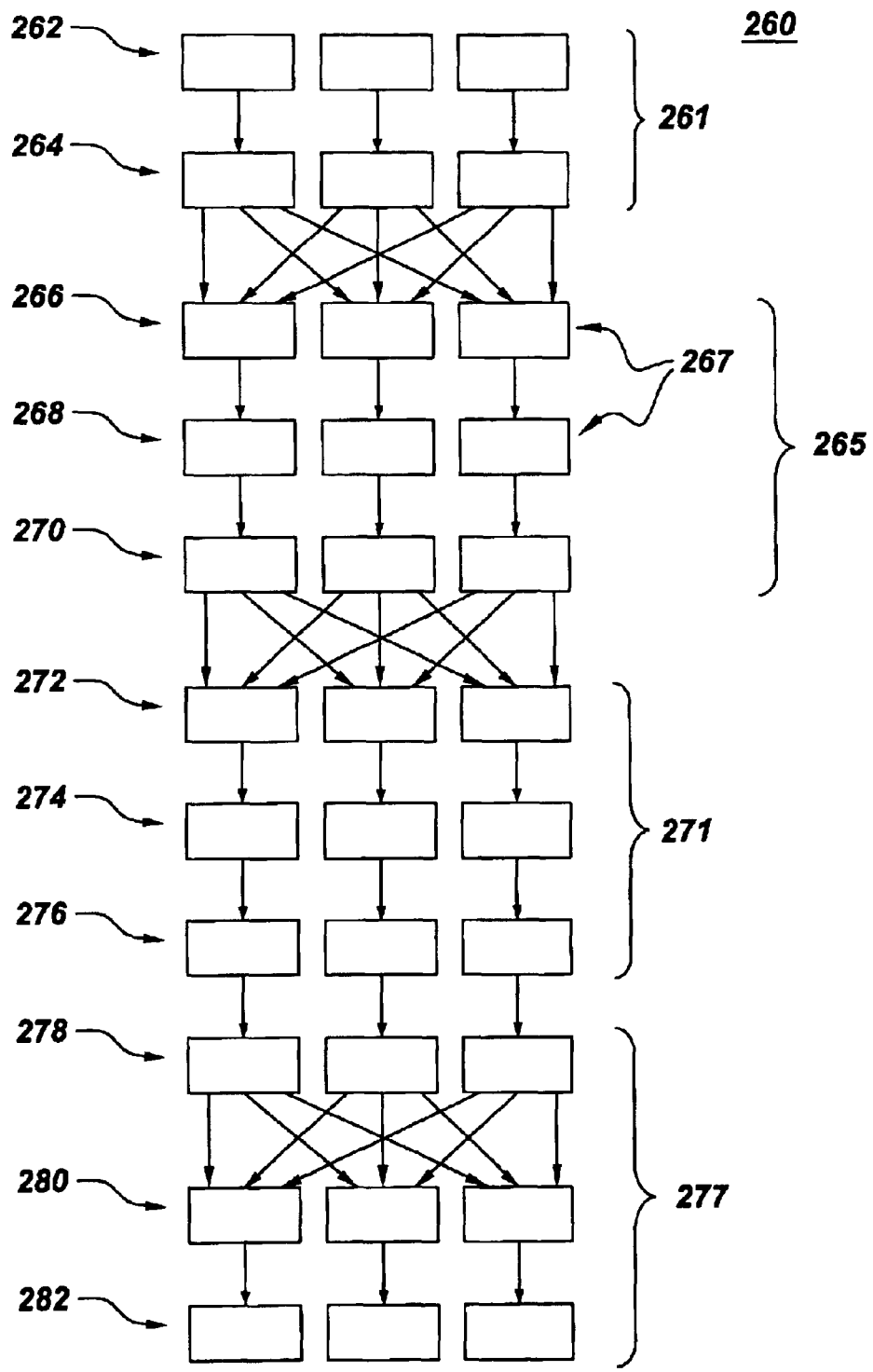
FIG. 12 is a flowchart corresponding to a Fourier Based Method for Optimal Reconstruction in Digital Tomosynthesis, executed by one embodiment of the digital tomosynthesis system of the present invention.

FIG. 12 is a flowchart 260 corresponding to the above-mentioned Fourier Based Method for Optimal Reconstruction in Digital Tomosynthesis that is executed by the digital tomosynthesis system 200. The flowchart 260 of Fourier Based Reconstruction shown in FIG. 12 comprises independent processing 261 of each projection image, independent processing 265 of each frequency component (which makes use of information about system geometry/focal spot positions 267), independent processing 271 of each horizontal slice through the object 114, and an optional iterative procedure 277 to improve reconstruction by incorporating information about support (or spatial extent) of the object 114, or other constraints.

As shown in FIG. 12, the above-mentioned processes 261, 265, 271, and 277 are executed as follows. While the following description relates to 2-dimensional processing of projection images and slices through the reconstructed volume, in one embodiment, a two-dimensional version of the Fourier Based Method for Optimal Reconstruction in Digital Tomosynthesis is used, as discussed herein above. This embodiment implies in particular that 1-dimensional Fourier transforms of corresponding cuts through the projection images and slices through the reconstructed volume are used.

Independent processing 261 of each projection image is executed by processes 262 and 264 as explained. Projection images are acquired 262 by the digital tomosynthesis system 200 for different focal spot positions. Next, the above-mentioned 2-dimensional Fourier transforms of each image are computed 264 by the digital tomosynthesis system 200.

Independent processing 265 of each frequency component is executed by processes 266, 267, 268, and 270 as explained. For each frequency, the Fourier coefficients of the corresponding frequency component are collected 266 for all projection images. Information about system geometry/focal spot positions 267 is utilized by processes 268 and 270, as explained. For each frequency, a system of linear equations which connects the Fourier coefficients of the projection images with certain characteristic vertical profiles of Fourier coefficients at corresponding frequencies are solved 268. These equations are determined by the focal spot positions 267 of the x-ray source 110 and the considered frequency. The corresponding frequencies at each height h of the object 114 are linked to the considered frequency in the projection images by the magnification factor associated with the corresponding height. For a given focal spot position of the x-ray source 110, a Fourier coefficient of the image captured at the detector 216 is a linear combination of the Fourier coefficients at the associated frequencies at horizontal slices through the imaged object 114. The complex weights in this linear combination are all of absolute value 1, but differ in phase. These weights are determined completely by the considered frequency, the focal spot position, and the height of the associated slice through the object 114, and are computed beforehand, if the focal spot positions are fixed in advance. For each frequency, and for each considered focal spot position, the collection of these weights (for all heights) in a vector represents the associated characteristic vertical profile.

The optimal vertical profile is determined 270 for each frequency, by computing the linear combination of the characteristic vertical profiles associated with the focal spot positions (for the corresponding frequency) weighted by the coefficients obtained by 268.

Independent processing 271 of each slice through the object 114 is executed by processes 272, 274, and 276, as explained. For every considered height for which a slice through the object 114 is being reconstructed by the digital tomosynthesis system 200, the Fourier coefficients of all frequencies (at the considered height) are collected 272 by determining the value of the corresponding optimal vertical profiles for all frequencies at the considered height.

For every considered height, the inverse Fourier transform is computed 274. The result is the optimal reconstruction 267 of the object 114 by the digital tomosynthesis system 200 at each of the considered heights, based only on the information given by the projections.

Using available additional information about the support (i.e., spatial extent) of the object 114, the reconstruction is restricted 278 to the support by setting all elements of the reconstruction which are located outside of the support (or bounding volume) to zero. Support is the region/volume where a function is not zero. In one embodiment, support is the volume where the object 114 is present as opposed to the region where the object 114 is not present. If the support of the object 114 is not known beforehand, then a so-called bounding volume can be used, which is a volume, defined by prior knowledge about the imaged object, which contains the object 114 (but which may be larger than the support of the object 114). Generally, the smaller the bounding volume is, the better the quality of the reconstruction of the object 114. In another embodiment, the additional constraint may include limiting the values in the reconstructed volume to the physically meaningful range, based on physical principles and prior knowledge about the imaged object.

The optional iterative procedure 277 is executed by processes 278, 280, and 282 as explained. For the following iterative update 277 of the reconstruction 260, a sufficient number of slices through the object 114 is reconstructed. For each focal spot position, the corresponding projection of the reconstructed object 114 is computed 280. This process 280 is accomplished by either computing the obvious line integrals along lines through the reconstructed object 114, or in the Fourier domain by first computing the Fourier transform of each reconstructed slice through the object 114 (after restricting the object 114 to the support, and/or applying other constraints), and then computing the scalar product of the vertical profile of the corresponding frequency components at different heights h with the characteristic vertical profiles, given by the focal spot position and the considered frequency.

The difference of the new projections with the original projection images is computed 282. Using this difference as input to the reconstruction algorithm (i.e., as input to process 264), the current estimate of the reconstructed object 114 is iteratively updated.

The Fourier Based Method for Optimal Reconstruction in Digital Tomosynthesis is applicable to both the 2-dimensional case (which corresponds to the special case of acquiring projection images by the x-ray source 110 following a linear trajectory), and a 3-dimensional case, which is of particular interest in the more general case where the x-ray source 110 follows a more general trajectory (i.e., not a linear trajectory) at a constant height above the detector. In the 2-dimensional case, all processes in the flowchart 260 of FIG. 12 are used in that exact order, but instead of processing projection images now "projection profiles" are used, where these projection profiles are obtained from the projection images by extracting the values of the images along certain lines, as discussed herein above. As described below, the 2 dimensional case is explained in detail, and an explanation of the 3-dimensional case follows. The 2-dimensional case accords computational efficiency over that of the 3 dimensional case, which may accord a superior image quality.

Figure 13:
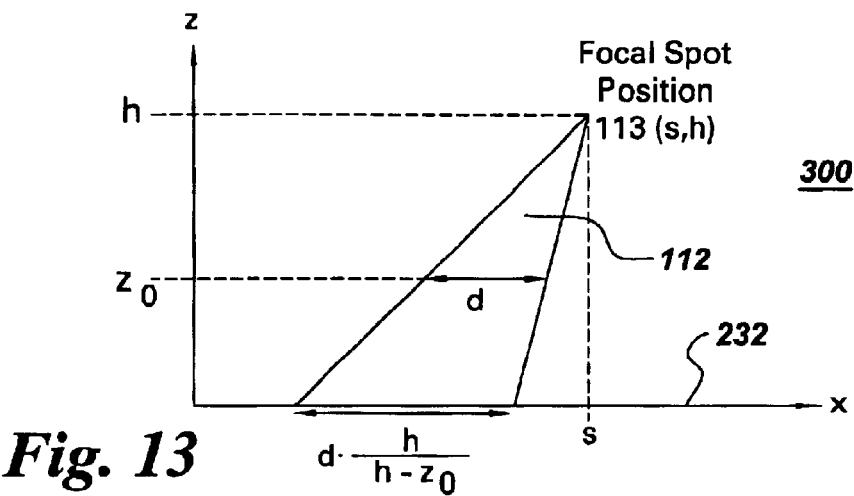
FIG. 13 shows a graph demonstrating a magnification factor associated with the fan beam projection in the digital tomosynthesis system of the present invention.

Referring now to the 2-dimensional case of the Fourier Based Method for Optimal Reconstruction in Digital Tomosynthesis, a horizontal slice through the object 114 is considered at a given height $z=z_o$ (as shown in FIG. 6, and more particularly in FIG. 13). The (locally varying) attenuation of the object 114 at this height $z_o$ is represented by a profile $o_z(x)$, in which x denotes a location along the horizontal axis. This profile can also be represented as a Fourier integral, $$o_z(x) = \int_w P_z(w) e^{iwx} dw, \quad (1)$$

where $P_z(w)$ denotes the Fourier transform of the profile $o_z(x)$. Simplifying assumptions include that the x-axis is infinite, i.e. $x \in R$, and that the profile or(x) is zero for all x for locations at which the object 114 is not present. The z-component is treated in the same way, thus simplifying the notation in the formal presentation.

A Single Fan Beam Projection

FIG. 13 shows a graph 300 demonstrating the above-mentioned magnification factor using a single fan beam projection. Referring now to FIG. 13, a considered focal spot position 113 has an x-component of s and a height h above the detector plane 232. Thus, the focal spot position 113 has the coordinates $(s,h)^T$. A fan bean projection of x-ray beam 112 with respect to this focal spot position 113 magnifies a slice through the object 114 at height z by a factor of $\kappa = h/(h-z)$, and maps the point (s,z) onto the point (s,0).

Therefore in the above-mentioned case, the horizontal profile $o_t(x)$ is mapped onto the following translated and scaled version of itself (which is observed at the detector 216):

$$o_z\left(\frac{1}{\kappa}x + \frac{\kappa-1}{\kappa}s\right) = \frac{h}{h-z} \int P_z\left(\frac{h}{h-z}w\right) \cdot e^{iw\frac{z}{h-z}s} e^{iwx} dw.$$

A more detailed derivation of this equation is provided herein below. The second expression (that is, the expression on the right hand side of the equal sign) represents the Fourier transform representation of the fan beam projection of the horizontal profile $o_z(x)$ at height z shown in FIG. 13. Therefore, the projection image (which comprises a super position of projections of slices of object 114 at all heights z) comprises Fourier coefficients of the form $$q_s(w) = \int_s P_z\left(\frac{h}{h-z}w\right) \cdot \frac{h}{h-z} \cdot e^{iw\frac{z}{z-h}s} dz. \quad (2)$$

Equation (2) links a single Fourier coefficient per slice (i.e., $p_z$) of the object 114 to a single Fourier coefficient of the projection (i.e., $q_z(w)$, where the subscript s denotes the specific x-ray source 110 position corresponding to the projection).

Reconstruction of $p_z$ from $q_s$

Equation (2) is a scalar product (with respect to the Hilbert space of square-integrable complex functions) of the functions $p_z$ $$p_z\left(\frac{h}{h-z}w\right)$$

and $$\left(\frac{h}{h-z} \cdot e^{iw\frac{z}{z-h}s}\right).$$

Thus, from these coefficients $q_s(w)$ (for different focal spot positions (113) s, i.e., for $S_n$, n=1 .. N) the component of the function $p_z$ $$p_z\left(\frac{h}{h-z}w\right)$$

(viewed as a function of height, z) which lies in the space spanned by the functions $e_n(z)=$ $$e_n(z) = \left(\frac{h}{h-z} \cdot e^{-iw\frac{z}{z-h}s_n}\right),$$

n=1 .. N is able to be determined. No other information is contained in these coefficients, and without any additional assumptions no additional information can be gained from the projection images.

In particular, the least squares approximation of $P_z$ $$p_z\left(\frac{h}{h-z}w\right)$$

(as a function of z) with respect to the space spanned by the functions $e_n$, (z) is given by $$p_z'\left(\frac{h}{h-z}w\right) = \sum_{n=1...N} c_n e_n(z) \quad (3)$$

where the coefficients $c_n$ are determined by the following system of linear equation (with complex coefficients)

$$\begin{pmatrix} E_{11} & \cdots & E_{1N} \\ \vdots & \ddots & \\ E_{N1} & & E_{NN} \end{pmatrix} \cdot \begin{pmatrix} c_1 \\ \vdots \\ c_N \end{pmatrix} = \begin{pmatrix} q_1 \\ \vdots \\ q_N \end{pmatrix}, \quad (4)$$

and the matrix elements $E_{mn}$ are given by $$E_{mn} = \int_z e_m(z)\overline{e_n(z)}dz = \int\int_z \left(\frac{h}{h-z}\right)^2 \cdot e^{iw\frac{z}{z-h}s_n} e^{-iw\frac{z}{z-h}s_n} dz \tag{5}$$

which can be readily evaluated for the predefined focal spot positions $s_n$, $s_m$.

This result (3) is optimal in the sense that it uses all of the available information, and does not create any additional information. Moreover, the matrix in equation (4) is (regular and therefore) invertible only if the functions $e_n(z)$ are linearly independent. If this is not the case, then a more careful (though still fairly basic) analysis is needed to determine the optimal approximation of $p_z$ $$p_z\left(\frac{h}{h-z}w\right).$$

An equation of type (4) is solved for each considered frequency w to get an optimal reconstruction of the structure of the object 114 across the range of frequencies w.

Introducing an Additional Constraint

The above-mentioned method determines an optimal reconstruction of the object 114 with respect to the considered Fourier domain representation. Since the extent of the object 114 is limited, upper and lower bounds (in both the x- and y-directions) can be assumed a *priori* such that the whole object 114 is contained in a volume defined by these bounds. The specific shape of the bounding volume is not constrained to be a cube, or even a regular shape. To obtain best results, however, the bounding volume should be as small as possible. The additional constraint may also include limiting the values in the reconstructed volume to the physically meaningful range, based on physical principles and prior knowledge about the imaged object.

In particular, the reconstructed object 114 (viewed as a function of (x,y,z)) is an element of the following two function spaces:

an element of the space S of functions which are zero outside of the bounding volume (and/or which satisfy other constraints), and an element of Q', the space of functions which generate exactly the set of given projection images, i.e., functions which satisfy equation (2), where the functions $q_{sn}$ (w) are completely determined by the projection images.

To be precise, Q' is a so-called affine space, and not a Hilbert space.

Alternating Projections Determine Optimal Reconstruction

The previously derived Fourier domain reconstruction gives rise to a function which is an element of the space Q', but generally this function will not be an element of S at the same time. The alternating projections approach comprises updating the solution such that alternatingly one of the two constraints is satisfied. Additionally, the alternating projections approach converges to a solution that meets both conditions.

Figure 14:
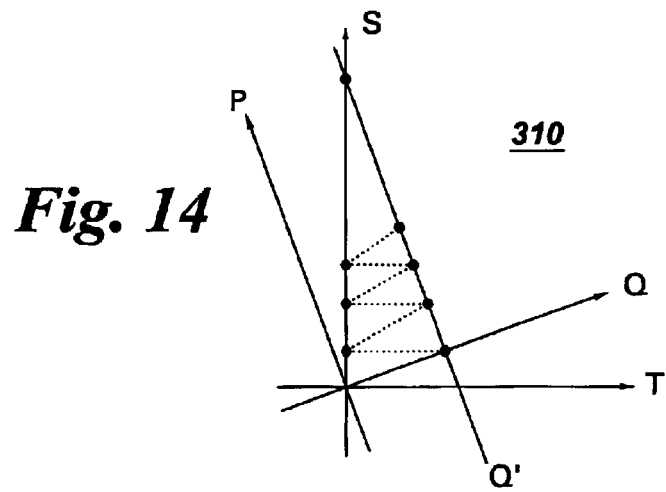
FIG. 14 shows a graph illustrating an alternating projections reconstruction approach in one embodiment of the digital tomosynthesis system of the present invention.

FIG. 14 shows a graph 310 illustrating the alternating projections approach. As shown in FIG. 14, an initial estimate of a solution is determined. This initial estimate is then updated as shown in the graph 310 of FIG. 14. In a first update, a function is added to the initial estimate that compensates for a non-zero component located outside of the bounding volume of the object 114. The result is an estimate that lies in the function space S. However, this in turn will lead to projections that do not coincide with the acquired projection images. A component that compensates for this deviation is then determined, and the newly updated estimate of the solution is now again an element of Q'. This approach converges quickly and is illustrated in FIG. 14.

In FIG. 14, P denotes the space of functions that lead to "zero" projections, i.e., functions that are not seen by the projection, while Q represents the space of functions that are completely determined by their projections. Similarly S denotes the space of functions that are zero outside of the defined bounding volume, while T is the space of functions that are zero inside the volume. The sought-for solution lies in S, while the original reconstruction only delivers a reconstruction in the space Q. The iterative procedure estimates the component of the solution which is in the space P, i.e., which cannot be observed by the projections.

The solution obtained with the procedure shown in FIG. 14 may still not be the accurate solution, i.e., the reconstructed three-dimensional structure of the imaged object may not be identical with the actual object, although FIG. 14 suggests otherwise. This is a consequence of the fact that the intersection of S and Q' will generally contain more than a single "point" (i.e., function).

Furthermore, determination of a solution which is an element of both Q' and S is not limited to the alternating projections method described herein above but can be found using other approaches.

Discretization of the Procedure

A discretization of the procedure is relatively straightforward. A natural discretization grid in x and y is typically determined by the pixel grid of the digital detector 216 (FIGS. 1, 3 and 4). Employing the discrete Fourier transform (in x/y) leads to periodic functions (if the functions are interpreted to be defined even outside of the considered interval). Thus, care has to be taken when choosing the interval in which the functions are defined in order to fully use the constraint that the object is zero outside of some predefined volume surrounding the object 114. On the other hand, the discretization grid in the z component does not depend on the spacing of the detector 216 grid. A suitable spacing in z may be chosen as a function of the maximum projection angle (for larger projection angles, a finer discretization in z may be needed). Because of the inherent magnification factor associated with different horizontal planes through the image object, it may be advantageous to use a discretization of the volume as illustrated in FIG. 7, where the x/y (i.e, horizontal) spacing of the grid within each horizontal slice is adjusted according to the corresponding magnification factor.

Derivation of the Fourier Based Method for Optimal Reconstruction in Digital Tomosynthesis The following is a discussion of the derivation of the above-mentioned Fourier Based Method for Optimal Reconstruction in Digital Tomosynthesis.

Basic Principle

To derive the Fourier Based Method for Optimal Reconstruction in Digital Tomosynthesis, assume at first a parallel projection scenario (this is in contrast to the fan beam projection scenario encountered in practice), and that the x-ray source 110 moves along a trajectory 212 parallel to the detector plane 232. Moreover, the 2-dimensional case is presented, which generalizes to the 3-dimensional case.

Figure 15:
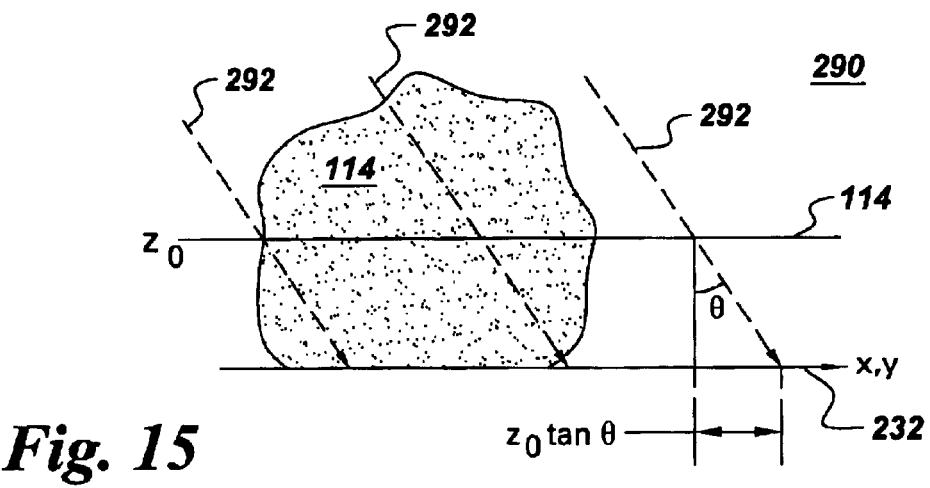
FIG. 15 is a diagram illustrating a parallel beam projection case useful in explaining the Fourier Based Reconstruction Technique used in one embodiment of the present invention.

FIG. 15 is a diagram 290 showing a 2-dimensional object imaging arrangement and coordinate system. More particularly, FIG. 15 is a diagram illustrating a parallel projection case useful for the derivation of the Fourier Based Reconstruction Technique. Using this assumption, several complications can be avoided here. That is, in FIG. 15, the magnification factor is 1, independent of the height, which eliminates the scaling of frequency as a function of the height. Thus, FIG. 15 illustrates an approximation of the real world case if the distance of the focal spot position of the x-ray source is large when compared to the height of the object.

The detector 216 (indicated in FIG. 15 as detector plane 232) is (without loss of generality) assumed to be horizontal at a height of z=0, and the imaged object 114 is located above the detector plane 232. In particular, assume that x-ray source 110 (not shown in FIG. 15) emits a beam of parallel x-rays 292 at an angle θ (as measured from the vertical axis z). A beam of parallel x-rays would be an ideal case in that x-ray source 110 would be an infinite distance from the detector plane 232, and the above-mentioned magnification factor would be equal to 1 (independent of the considered height).

Consider now a horizontal cut through the object at a given height $z=Z_o$. The (locally varying) attenuation of the object at this height can be represented by a profile $o_z(x)$, where x denotes the location along the horizontal axis. Furthermore, the profile can be represented as a Fourier integral, $$o_z(x) = \int_w p_z(w) e^{iwx} dw. \tag{6}$$

In particular an infinite x-axis, i.e. $x \in R$, is assumed and the profile $o_z(x)$ is considered to be zero for all x where the object 114 is not present. The z-component is treated in exactly the same way, which significantly simplifies the formal presentation.

The parallel projection (as shown in FIG. 15) maps the considered profile of the object 114 onto a translated (shifted) copy of itself, where the amount of the shift depends on the height z of the considered profile, and on the angle θ of the projection. In particular, for a projection angle θ (as measured from the vertical z) and for a height z of the considered cut through the object, the length of the shift is z tan θ. That is, the attenuation profile $o_z(x)$ at height z is mapped onto a "projection profile" $o_z$ (x−z tan θ).

For a single projection at angle θ, a superposition of projections of all horizontal slices through the considered object occurs (i.e., a superposition of appropriately shifted versions of profiles at all heights z occurs), and consequently the observed profile at the detector 216 is of the form $$P_\theta(x) = \int_z o_z(x - z\tan\theta) dz.$$

Inserting the Fourier representation (6) into this expression one obtains $$P_\theta(x) = \int_z \int_w p_z(w) e^{iwx} e^{iwz\tan\theta} dw dz.$$

Rewriting the foregoing expression in standard Fourier integral form yields $$P_\theta(x) = \int_w q_\theta(w) e^{iwx} dw,$$

where the Fourier coefficient $q_\theta(w)$ is of the form $$q_\theta(w) = \int_z p_z(w) e^{-iwz\tan\theta} dz. \tag{7}$$

Therefore the Fourier coefficients $q_\theta(w)$ of the projection image $P_\theta(x)$ are linked to the Fourier coefficients $p_z(w)$ of all horizontal slices through the imaged object 114 by equation (7). In particular, the Fourier coefficients $q_\theta(w)$ at the frequency w are a function only of the Fourier coefficients of the horizontal object 114 slices at the exact same frequency.

Optimal Reconstruction of Fourier Coefficients of Object "Slices" (at a Particular Frequency)

Assume that there are projections at several angles $\theta_n$, n=1 . . N. Then the Fourier coefficient of the different projection images admit a representation of the form $$q_{\theta_n}(w) = \int_z p_z(w) e^{-iwz\tan\theta_n} dz, \tag{8}$$

an expression which represents essentially a scalar product with respect to the Hilbert space of square-integrable complex functions. In particular, from these coefficients the component of the function $p_z(w)$ which lies in the space spanned by the functions $e^{iwz \tan \theta}$, n=1 . . N is determined. No other information is contained in these coefficients, and without any additional assumptions no additional information can be gained from the projection images.

The principle of determining an optimal estimate of $p_z(w)$ from the scalar products of the form (8) is now explained.

From basic linear algebra, a least squares approximation of a real-valued (column) vector p is recovered from a set of scalar products $q_n = e_n^T p$, where the vectors $e_n$ and the values $q_n$ are known. In particular, $$\left( \begin{pmatrix} e_1^T \\ \vdots \\ e_N^T \end{pmatrix} \cdot (e_1 \; \ldots \; e_N) \right) \begin{pmatrix} c_1 \\ \vdots \\ c_N \end{pmatrix} = \begin{pmatrix} q_1 \\ \vdots \\ q_N \end{pmatrix}. \tag{9}$$

The $e_n$ are column vectors, while $c_n$ and $q_n$ are scalars, and the raising to the T power denotes the transposed vector.

Solving this system of linear equations leads to the solution vector c such that $$p' = (e_1 \; \ldots \; e_N) \cdot \begin{pmatrix} c_1 \\ \vdots \\ c_N \end{pmatrix} = \sum_{n=1\ldots N} c_n e_n$$

is the least squares approximation of p with respect to the space spanned by the vectors $e_n$. This result is optimal in the sense that it uses all of the available information, and does not create any additional information. The matrix in equation (9) is (regular and therefore) invertible only if the vectors $e_n$ are linearly independent. If this was not the case, then a more careful analysis is needed to determine the optimal approximation of p.

In the Fourier based method for optimal reconstruction in digital tomosynthesis, a similar situation exists, but the Fourier Based Method for Optimal Reconstruction in digital tomosynthesis deals with complex valued functions instead of real-valued vectors, and considers the Hilbert space of square integrable complex functions instead of a finite dimensional vector space. Specifically, the values $q_n$ are here replaced by $q_\theta$, (w), and the vectors $e_i$ are replaced by the functions $e^{iwt \tan \theta}$. Exactly in the same way as outlined above, a matrix is obtained whose elements are now given by the pairwise scalar products of the functions $e^{iwt \tan \theta}$, i.e., element (m,n) of this matrix is of the form $$\int_{z'} e^{iwz\tan\theta_m} e^{-ixz\tan\theta_n} dz,$$

which is readily evaluated for the predefined projection angles $\theta_n$. Solving the resulting system of linear equations (with complex coefficients) provides a set of coefficients $c_1 \ldots, c_N$, and $$p'_z(w) = \sum_n c_n \cdot e^{iwz\tan\theta_n}$$

represents the optimal reconstruction of the Fourier coefficients $p_z(w)$ at the (fixed) frequency w for all heights z (i.e., $p_z(w)$, with w fixed, is here interpreted as a function of z). A similar system of linear equations is solved for every considered frequency w.

Connection to the Fourier Slice Theorem

One interpretation of Equation (7) is computing the Fourier transform coefficient of the function $p_z(w)$ (considered as a function of the height z for a fixed frequency w) associated with the frequency wtan θ. This implies also that $q_\theta(w)$ is the Fourier coefficient associated with frequency (w,wtanθ) of the 2-dimensional Fourier transform of the 2-dimensional object $o_z(w)=o(z, w)$. This relationship is essentially a reformulation of the Fourier slice theorem, which states that the one-dimensional Fourier transform of the (parallel) projection is equal to the central slice, at angle θ, of the two-dimensional Fourier transform of the object.

Generalization to the 3-Dimensional Case

A generalization of the previously developed 2-dimensional the Fourier based method for optimal reconstruction in digital tomosynthesis from parallel projections to the 3-dimensional case is now explained.

Because a horizontal slice through the imaged object 114 as well as its projection onto the detector 216 are 2-dimensional, the standard 2-dimensional Fourier transform is utilized. The Fourier basis functions in this case are given by the Cartesian product of the 1-dimensional Fourier basis functions, i.e., the Fourier coefficients are now indexed by both, a frequency in x-direction and a frequency in y-direction. As in the 2-dimensional case, a slice through the object 114 is mapped onto a translated version of itself.

This translation is split into a x- and a y-component, and the further generalization of the 2-dimensional case follows. Again the Fourier coefficients of the projections are linked to the Fourier coefficients of all horizontal slices through the object 114 by an equation of the type (7), and a system of linear equations is solved to determine the optimal Fourier coefficients of the object "slices" from the Fourier coefficients of the projections.

As discussed earlier, in the case of a linear trajectory of the x-ray source 110 at a constant height above the detector plane, this 3-dimensional process is not needed, but it can optionally be employed in that situation. However, as discussed herein above, the two-dimensional reconstruction affords computational advantages compared to the three-dimensional reconstruction.

Generalization to Fan Beam Projection

Assume that the considered focal spot position has a x-component of s and a height h above the detector 216 (i.e., it has the coordinates $(s,h)^T$). A fan beam projection with respect to this focal spot position magnifies a slice through the object 114 at height z by a factor of $\kappa=h/(h-z)$, and maps the point (s,z) onto the point (s,0). Therefore in this case the horizontal profile $o_z(x)$ is mapped onto the following translated and scaled version of itself:

$$o_z\left(\frac{1}{K}x + \frac{K-1}{K}s\right) = o_z\left(\left(1-\frac{z}{h}\right)x + \frac{z}{h}s\right) = \int p_z(w)e^{iw(1-\frac{z}{h})x}e^{iw\frac{z}{h}s}dw.$$

The above-mentioned expression was obtained by rewriting $o_z(x)$ in terms of its Fourier transform (similar to equation (6)). Performing a change of variables yields $$o_z\left(\frac{1}{\kappa}x + \frac{\kappa-1}{\kappa}s\right) = \frac{h}{h-z}\int p_z\left(\frac{h}{h-z}w\right)e^{iw\frac{z}{h-z}s}e^{iwx}dw.$$

The above-mentioned expression represents the Fourier transform representation of the fan beam projection of the horizontal profile $o_z(x)$ at height z. It follows immediately that the projection image (which comprises a superposition of projections of slices at all heights z) has Fourier coefficients of the form $$q_s(w) = \int_z p_z\left(\frac{h}{h-z}w\right) \cdot \frac{h}{h-z} \cdot e^{iw\frac{z}{z-h}s}dz. \quad (10)$$

This expression corresponds to equation (7) for the parallel projection case. Now, as in the parallel projection case, this equation links a single Fourier coefficient per slice to a single Fourier coefficient of the projection. However, due to the magnification property of the fan beam projection these Fourier coefficients are not all associated with the same frequency w. Further, this equation can not be interpreted as a Fourier transform, although it can certainly be considered to be an approximation if z is much smaller than h (i.e., if the maximum height of the object is small with respect to the minimum height of the focal spot of the x-ray source 110). Note that equation (10) derived herein above corresponds exactly to equation (2) that was given earlier without detailed derivation.

Introducing an Additional Constraint

An optimal reconstruction of the object 114 is obtained as described herein above for a reconstruction of Fourier coefficients at a single frequency (and for all heights z, refer to equation (8)), which is performed for all frequencies.

In general, though, the extent of the object 114 is limited, and a *priori* lower and upper bounds (in both the x- and y-direction) are assumed such that the whole object 114 is contained in the volume between these bounds. That means that $o_z(x)$ is zero outside of a given interval. From the fact that $o_z(x)$ is essentially the Fourier transform of $p_z(w)$ it follows that $p_z(w)$ is bandlimited. This implies in particular that $p_z(w)$, viewed as a function of the frequency w, is smooth. The values $p_z(w)$ and $p_z(w+\delta_w)$ are not unrelated anymore (which seemed to be the case earlier, when equation (8) was derived). In particular, the spectrum $p_z(w)$ is already completely determined by equally spaced samples $p_z(w_k)$. From these samples the function $p_z(w)$ is recovered for all w, by interpolating with a suitable version of the sinc $$\left(\text{i.e., } \frac{\sin x}{x}\right)$$

function. This constraint will in general not be satisfied by the previously reconstructed functions $p_z(w)$, where essentially separate and independent relationships for every frequency w were used. This is a consequence of the fact that only partial information about the object 114 was used, namely the Fourier representation of its projections.

This new spatial constraint (and/or other constraints, as explained above) is used as follows. It can be seen that an approach using the above-mentioned alternating projections lends itself to iteratively reconstruct the object 114 such that both types of constraint (Fourier and spatial) are met.

In particular, the reconstructed object 114 is an element of the following two function spaces:

the space S of functions which are zero outside of the bounding volume (and/or which satisfy other constraints), and Q', the space of functions which "generate" exactly the set of projections, i.e., which satisfy equation (2), where the functions $q_z(w)$ are completely determined by the projection images. (To be precise, Q' is an affine space, and not a Hilbert space).

The previously derived reconstruction gives rise to a function which is an element of the space Q, but generally this function will not be an element of S at the same time.

The above-mentioned alternating projections approach updates the solution such that alternatingly one of the two constraints is satisfied. The alternating projections approach converges to a solution that meets both conditions.

Other Generalizations

The relationship between the characteristic vertical profile associated with each frequency and each focal spot position, and the corresponding vertical profile of Fourier coefficients that can be obtained from Fourier transforms of slices through the object at different heights, is still satisfied even with only a single focal spot position. If there is an initial reconstruction of the object (which may also be zero everywhere, when no initial reconstruction is available), the corresponding vertical profiles (for all frequencies) of this reconstructed object are obtained, and the reconstructed object is then updated such that the vertical profiles are optimal (with respect to that focal spot, and for all frequencies). This corresponds to the case described herein above in which only the Fourier space information from the projection images is included, the only difference being that there is only a single focal spot. This step is then repeated for each of the focal spots, even if there is more than one focal spot. To obtain the "optimal" reconstruction, this step is repeated over and over again, while stepping sequentially through the different focal spots. Eventually this approach converges. Thus, the reconstruction method of the present invention can even be generalized to other scenarios, in which the focal spots are not necessarily located at the same height (for example in the embodiment of the present invention shown in FIG. 9), and is particularly useful to improve upon an already existing estimate of the reconstruction. Thus, while the above-mentioned Fourier Based Reconstruction Method is based upon the general idea of using and estimating vertical profiles of Fourier coefficients at corresponding frequencies, and makes efficiently use of these relationships, this same principle can be used in more general scenarios, in particular for system geometries where not all focal spot locations are located at the same height above the detector. Furthermore, in the framework of the embodiment of the present invention shown in FIG. 9, the iteration steps using the Fourier domain information can be alternatingly used with above mentioned iteration steps using the information about the support of the imaged object, or the bounding volume, to obtain a generalization of the alternating projections approach.

In another embodiment, the Fourier based method for optimal reconstruction in digital tomosynthesis may be used to reconstruct only certain frequency components in the imaged volume. For example, if only edges of the imaged volume are of interest, then one might want to reconstruct only components corresponding high frequencies, since edges are characterized mostly by their high frequency content. Furthermore, since the Fourier based method for optimal reconstruction in digital tomosynthesis effectively decouples different frequencies in the imaged volume, and allows to reconstruct components at specific frequencies individually, one can also use the method of the present invention to reconstruct components at specific frequencies, while all other components can be reconstructed with a different reconstruction method.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A digital tomosynthesis system adapted to acquire a plurality of projection radiographs of an object and comprising:

an x-ray source adapted to emit a beam of x-rays;

a digital detector disposed in a spatial relationship to the x-ray source relative to the object; and a processor coupled to said x-ray source and said detector adapted to control said x-ray source and process data received from said detector such that projection radiographs are acquired at different positions of the focal spot of the x-ray source relative to said object along a linear trajectory of the x-ray source, wherein the x-ray source moves in a trajectory at a constant distance from the detector.

2. The digital tomosynthesis system as in claim 1, wherein the detector comprises rows of pixels and the columns of pixels configured in a grid, and the x-ray source moves in a trajectory parallel to either one of the rows or the columns.

3. The digital tomosynthesis system as in claim 1, wherein the focal spot of the x-ray source is provided at a plurality of positions located in a plane parallel to the detector.

4. The digital tomosynthesis system as in claim 2, wherein for each of the rows or columns of pixels there is a uniquely defined plane in 3-dimensional space such that for any focal spot position of the x-ray source on the trajectory, structures of the object in the plane are projected onto either one of the pixel rows or columns.

5. The digital tomosynthesis system as in claim 1 wherein said detector comprises pixels organized into rows and columns, wherein a focal spot of the x-ray source moves relative to the detector in a linear trajectory parallel to one of either the rows of pixels or the columns of pixels.

6. The digital tomosynthesis system as in claim 1, wherein the processor further independently reconstructs 3-dimensional structures provided in logical planes of an object by computing 2-dimensional reconstructions of information about the structures in said planes of said object from information provided in the acquired projection radiographs.

7. A digital tomosynthesis system as in claim 6, wherein the 2-dimensional reconstructions are assembled to form a 3-dimensional volumetric reconstruction of the object.

8. A digital tomosynthesis system as in claim 7, wherein the focal spot positions of the x-ray source are located at a constant height above the detector, and wherein the 2-dimensional reconstructions are computed by determining mathematical relationships between Fourier Transforms of logical slices through the object with Fourier Transforms of projection images of the object.

9. The digital tomosynthesis system as in claim 3, wherein reconstructed 3-dimensional information is determined based upon interpolated, one-dimensional functions.

10. The digital tomosynthesis system as in claim 3, wherein reconstructed 3-dimensional information is determined based upon interpolated, one-dimensional functions.

11. The digital tomosynthesis system as in claim 3, wherein the structures of the object at a height are decomposed into linear combinations of sinusoidal structures, said sinusoidal structures corresponding to different heights within the object being superimposed in the projection radiographs, and said structures of the object being reconstructed based upon the projection radiographs.

12. The digital tomosynthesis system as in claim 11, wherein each sinusoidal structures at each height produces a sinusoidal structure in the projection image, and for different positions of the focal spot of the x-ray source, the frequency of the sinusoidal structure in the projection image remains constant and the phase shift of the sinusoidal structure in the projection image varies based on the different positions of the focal spot of the x-ray source and the height of the sinusoidal structure, said sinusoidal structures at different heights being reconstructed from the sinusoidal structures within the projection images.

13. The digital tomosynthesis system as in claim 4, wherein reconstructed 3-dimensional information is determined based upon interpolated, one-dimensional functions.

14. A method of digital tomosynthesis using a system having an x-ray source and a digital detector, comprising:
using the detector to acquire projection radiographs of an object based on x-ray beams emitted by the x-ray source; and
controlling said x-ray source and processing data received from said detector such that projection radiographs are acquired at different positions of a focal spot of the x-ray source relative to said detector along a linear trajectory of the x-ray source, wherein the x-ray source moves in a linear trajectory located at a constant distance from the detector.

15. The method as in claim 14, wherein the x-ray source moves in a linear trajectory relative to and parallel to either rows of pixels or columns of pixels provided in the detector.

16. The method as in claim 14, further comprising:
providing the focal spot of the x-ray source at a plurality of positions located in a plane parallel to the detector.

17. The method as in claim 15, wherein for each of the rows or column of pixels there is a uniquely defined, plane in 3-dimensional space such that for any focal spot position of the x-ray source on the trajectory, structures of the object in the plane are projected onto said pixel row or column, and a 3-dimensional image of the structures of the object is reconstructed from the projections onto either one of the pixel rows or columns.

18. The method as in claim 15, further comprising:
reconstructing independently 3-dimensional structures provided in planes of an object by computing 2-dimensional reconstructions of information about the structures in said planes of said object from information provided in the acquired projection radiographs.

19. The method as in claim 18, further comprising:
assembling the 2-dimensional reconstructions to form a 3-dimensional volumetric reconstruction of the object.

20. The method as in claim 14, further comprising:
decomposing the structures of the object at a height into linear combinations of sinusoidal structures, said sinusoidal structures corresponding to different heights within the object being superimposed in the projection radiographs, and said structures of the object being reconstructed based upon the projection radiographs.

21. The method as in claim 20, further comprising
producing by each sinusoidal structure at each height a sinusoidal structure in the projection image, and for different positions of the focal spot of the x-ray source, the frequency of the sinusoidal structure in the projection image remains constant and the phase shift of the sinusoidal structure in the projection image varies based on the different positions of the focal spot of the x-ray source and the height of the sinusoidal structure, said sinusoidal structures at different heights being reconstructed from the sinusoidal structures within the projection images.

22. The method as in claim 17, further comprising:
determining the reconstructed 3-dimensional information based upon one-dimensional functions.

* * * * *